(12) United States Patent
Braun et al.

(10) Patent No.: US 7,958,589 B2
(45) Date of Patent: Jun. 14, 2011

(54) TOOTHBRUSHES

(75) Inventors: Phillip M. Braun, Exeter, RI (US);
William R. Brown, Jr., Peabody, MA
(US); Alexander T. Chenvainu,
Sudbury, MA (US); **Thomas A.
Christman**, Lexington, MA (US)

(73) Assignee: The Gillette Company, Boston, MA
(US)

( * ) Notice: Subject to any disclaimer, the term of this
patent is extended or adjusted under 35
U.S.C. 154(b) by 0 days.

(21) Appl. No.: 12/483,838

(22) Filed: Jun. 12, 2009

(65) Prior Publication Data
US 2009/0282628 A1    Nov. 19, 2009

Related U.S. Application Data

(63) Continuation of application No. 10/364,148, filed on Feb. 11, 2003.

(51) Int. Cl.
A46B 13/02    (2006.01)
(52) U.S. Cl. ............... 15/110; 15/167.1; 15/22.1; 15/28
(58) Field of Classification Search .................... 15/110, 15/111, 167.1, 22.1, 28
See application file for complete search history.

(56) References Cited

U.S. PATENT DOCUMENTS

| | | | |
|---|---|---|---|
| 0,034,109 A | 1/1862 | Fanshaw et al. | |
| 0,116,030 A | 6/1871 | Devines | |
| 0,218,431 A | 8/1879 | Dunham | |
| 0,411,910 A | 10/1889 | Van Horne | |
| 0,742,639 A | 10/1903 | Harlan | |
| 0,907,842 A | 12/1908 | Meuzies | |
| 0,915,251 A | 3/1909 | Vanderslice | |
| 1,006,630 A | 10/1911 | Clarke | |
| 1,191,556 A | 7/1916 | Blake | |
| 1,251,250 A | 12/1917 | Libby | |
| 1,268,544 A * | 6/1918 | Cates | 15/110 |
| 1,297,272 A | 3/1919 | Pollock | |
| 1,526,267 A | 2/1925 | Dessau | |
| 1,578,074 A | 3/1926 | Chandler | |
| 1,588,785 A | 6/1926 | Van Sant | |
| 1,598,224 A | 8/1926 | Van Sant | |
| 1,705,249 A | 3/1929 | Henry | |
| 1,720,017 A | 7/1929 | Marshall | |
| 1,863,389 A | 5/1931 | Anderson | |

(Continued)

FOREIGN PATENT DOCUMENTS

CN    1248151    3/2000

(Continued)

OTHER PUBLICATIONS

PCT International Search Report, Dated Jul. 5, 2004, for PCT/US2004/002401.

(Continued)

*Primary Examiner* — Laura C Guidotti
(74) *Attorney, Agent, or Firm* — Calfee, Halter & Griswold LLP

(57) ABSTRACT

Toothbrush heads, e.g., for power toothbrushes, are provided. An embodiment of the toothbrush heads include a support structure, a plurality of upstanding accurate members extending upward from a surface of the support structure forming an open center area, a second cleaning element disposed within the open center area and plurality of bristle tufts extending from the support structure and at least partially surrounding at least one of the plurality of arcuate segments

55 Claims, 12 Drawing Sheets

U.S. PATENT DOCUMENTS

| | | |
|---|---|---|
| 1,833,555 A | 11/1931 | Bell et al. |
| 1,852,480 A | 4/1932 | Ruetz |
| 1,861,347 A | 5/1932 | Johnson |
| 1,868,893 A | 7/1932 | Gentle |
| 1,901,230 A | 3/1933 | Duey |
| 1,910,414 A | 5/1933 | Varga |
| 1,924,152 A | 8/1933 | Coney et al. |
| 1,935,417 A | 11/1933 | Gavney et al. |
| 1,963,389 A | 6/1934 | Vardeman |
| 1,965,009 A | 7/1934 | Stevens |
| 1,993,662 A | 3/1935 | Green |
| 2,042,239 A | 5/1936 | Planding |
| 2,059,914 A | 11/1936 | Rosenberg |
| 2,088,839 A | 8/1937 | Coney et al. |
| 2,093,007 A | 9/1937 | Chott |
| 2,117,174 A | 5/1938 | Jones |
| 2,219,753 A | 5/1938 | Seguin |
| 2,129,082 A | 9/1938 | Byrer |
| 2,139,245 A | 12/1938 | Ogden |
| 2,146,455 A | 2/1939 | Tepper |
| 2,189,175 A | 2/1940 | Jackson |
| 2,206,726 A | 7/1940 | Lasater |
| 2,220,053 A | 10/1940 | Pruner |
| 2,225,331 A | 12/1940 | Campbell |
| 2,226,663 A | 12/1940 | Hill et al. |
| 2,246,867 A | 6/1941 | Nash |
| 2,279,355 A | 4/1942 | Wilensky |
| 2,326,632 A | 8/1943 | Friedman |
| 2,328,998 A | 9/1943 | Radford |
| 2,334,796 A | 11/1943 | Steinmetz et al. |
| 2,364,205 A * | 12/1944 | Fuller ........................ 601/141 |
| 2,443,461 A | 6/1948 | Kempster |
| 2,512,059 A | 6/1950 | Haeusser |
| 2,534,086 A | 12/1950 | Vosbikian et al. |
| 2,545,814 A | 3/1951 | Kempster |
| 2,637,870 A | 5/1953 | Cohen |
| 2,702,914 A | 3/1955 | Kittle |
| 2,757,668 A | 8/1956 | Meyer-Saladin |
| 2,789,352 A | 4/1957 | Wiseman |
| 2,815,601 A | 12/1957 | Hough, Jr. |
| 2,819,482 A | 1/1958 | Applegate |
| 2,987,742 A | 6/1961 | Kittle et al. |
| 3,016,554 A | 1/1962 | Peterson |
| 3,103,027 A | 9/1963 | Birch |
| 3,110,052 A | 11/1963 | Whitman |
| 3,113,546 A | 12/1963 | Mountcastle |
| 3,128,487 A | 4/1964 | Vallis |
| 3,181,193 A | 5/1965 | Nobles et al. |
| 3,195,537 A | 7/1965 | Blasi |
| 3,196,299 A | 7/1965 | Kott |
| 3,258,805 A | 7/1966 | Rossman |
| 3,295,156 A | 1/1967 | Brant |
| 3,302,230 A | 2/1967 | Poppelman |
| 3,316,576 A | 5/1967 | Urbush |
| 3,327,339 A | 6/1967 | Lemelson |
| 3,403,070 A | 9/1968 | Lewis, Jr. |
| 3,411,979 A | 11/1968 | Lewis, Jr. |
| RE26,688 E | 10/1969 | Lemelson |
| 3,491,396 A | 1/1970 | Eannarino et al. |
| 3,553,759 A | 1/1971 | Kramer et al. |
| 3,613,143 A | 10/1971 | Muhler et al. |
| 3,641,610 A | 2/1972 | Lewis et al. |
| 3,677,264 A | 7/1972 | Brockman |
| 3,939,522 A | 2/1976 | Shimizu |
| 3,959,842 A | 6/1976 | Alley |
| 3,969,783 A | 7/1976 | Shipman |
| 3,992,747 A | 11/1976 | Hufton |
| 4,033,008 A | 7/1977 | Warren et al. |
| 4,115,893 A | 9/1978 | Nakata et al. |
| 4,128,910 A | 12/1978 | Nakata et al. |
| 4,263,691 A | 4/1981 | Pakarnseree |
| 4,277,862 A | 7/1981 | Weideman |
| 4,288,883 A | 9/1981 | Dolinsky |
| 4,356,585 A | 11/1982 | Protell et al. |
| 4,391,951 A | 7/1983 | Scheetz |
| 4,403,623 A | 9/1983 | Mark |
| 4,472,853 A | 9/1984 | Rauch |
| 4,476,280 A | 10/1984 | Poppe et al. |
| 4,480,351 A | 11/1984 | Koffler |
| 4,525,531 A | 6/1985 | Zukosky et al. |
| 4,538,631 A | 9/1985 | Prince |
| 4,573,920 A | 3/1986 | d'Argembeau |
| 4,585,416 A | 4/1986 | DeNiro et al. |
| 4,603,166 A | 7/1986 | Poppe et al. |
| 4,616,064 A | 10/1986 | Zukosky et al. |
| 4,617,342 A | 10/1986 | Poppe et al. |
| 4,617,694 A | 10/1986 | Bori |
| 4,623,495 A | 11/1986 | Degoix et al. |
| 4,672,706 A | 6/1987 | Hill |
| 4,691,405 A | 9/1987 | Reed |
| 4,720,489 A | 1/1988 | Shander |
| 4,763,380 A | 8/1988 | Sandvick |
| 4,802,255 A | 2/1989 | Breuer et al. |
| 4,812,070 A | 3/1989 | Marty |
| 4,827,551 A | 5/1989 | Maser et al. |
| 4,854,870 A | 8/1989 | Kofod |
| 4,866,806 A | 9/1989 | Bedford |
| 4,929,180 A | 5/1990 | Moreschini |
| 4,974,615 A | 12/1990 | Doundoulakis |
| 5,005,246 A | 4/1991 | Yen-Hui |
| 5,027,463 A | 7/1991 | Daub |
| 5,032,082 A | 7/1991 | Herrera |
| 5,040,260 A | 8/1991 | Michaels |
| 5,058,230 A | 10/1991 | Hodosh et al. |
| 5,137,039 A | 8/1992 | Klinkhammer |
| 5,211,494 A | 5/1993 | Baijnath |
| 5,226,197 A | 7/1993 | Nack et al. |
| 5,249,327 A | 10/1993 | Hing |
| 5,323,795 A | 6/1994 | Berens |
| 5,335,389 A | 8/1994 | Curtis et al. |
| 5,345,644 A | 9/1994 | Gueret |
| 5,347,676 A | 9/1994 | Saitoh |
| 5,360,339 A | 11/1994 | Rosenberg |
| 5,378,153 A | 1/1995 | Giuliani et al. |
| 5,392,482 A | 2/1995 | Drulias et al. |
| 5,440,774 A | 8/1995 | Cole |
| 5,467,495 A | 11/1995 | Boland et al. |
| 5,491,863 A | 2/1996 | Dunn |
| 5,497,526 A | 3/1996 | Klinkhammer |
| 5,528,793 A | 6/1996 | Schbot |
| 5,535,474 A | 7/1996 | Salazar |
| 5,564,150 A | 10/1996 | Ciccotelli |
| 5,584,690 A | 12/1996 | Maassarani |
| D378,166 S | 2/1997 | Savitt et al. |
| 5,604,951 A | 2/1997 | Ship |
| 5,648,394 A | 7/1997 | Boxall et al. |
| 5,669,097 A | 9/1997 | Klinkhammer |
| 5,689,850 A | 11/1997 | Shekalim |
| 5,700,146 A | 12/1997 | Kucar |
| 5,711,759 A | 1/1998 | Smith et al. |
| 5,735,011 A | 4/1998 | Asher |
| 5,758,383 A | 6/1998 | Hohlbein |
| 5,799,353 A | 9/1998 | Oishi et al. |
| 5,806,127 A | 9/1998 | Samoil et al. |
| 5,813,079 A | 9/1998 | Halm |
| 5,851,551 A | 12/1998 | Tseng et al. |
| 5,860,183 A | 1/1999 | Kam |
| 5,864,915 A | 2/1999 | Ra |
| 5,878,459 A | 3/1999 | McParland |
| 5,896,614 A | 4/1999 | Flewitt |
| 5,903,949 A | 5/1999 | Halm |
| 5,926,900 A | 7/1999 | Bennett |
| D413,384 S | 8/1999 | Hanley et al. |
| D413,385 S | 8/1999 | Hanley et al. |
| 5,930,860 A | 8/1999 | Shipp |
| 5,946,758 A | 9/1999 | Hohlbein et al. |
| 5,946,759 A | 9/1999 | Cann |
| 5,966,771 A | 10/1999 | Stoud |
| 5,980,542 A | 11/1999 | Saldivar |
| 5,987,688 A | 11/1999 | Roberts et al. |
| 5,991,958 A | 11/1999 | Hohlbein |
| 5,991,959 A | 11/1999 | Raven et al. |
| 6,003,189 A | 12/1999 | Falleiros |
| 6,021,541 A | 2/2000 | Mori et al. |
| 6,032,322 A | 3/2000 | Forsline |
| 6,041,467 A | 3/2000 | Roberts et al. |
| 6,044,514 A | 4/2000 | Kaneda |

| Patent No. | Date | Name |
|---|---|---|
| 6,065,890 A | 5/2000 | Weitz |
| 6,067,684 A | 5/2000 | Kweon |
| 6,073,299 A | 6/2000 | Hohlbein |
| 6,077,360 A | 6/2000 | Takashima |
| 6,092,252 A | 7/2000 | Fischer et al. |
| 6,101,659 A | 8/2000 | Halm |
| 6,108,849 A | 8/2000 | Weihrauch |
| 6,108,854 A | 8/2000 | Dingert |
| 6,115,870 A | 9/2000 | Solanki et al. |
| 6,126,533 A | 10/2000 | Johnson et al. |
| 6,138,316 A | 10/2000 | Weihrauch |
| 6,146,140 A | 11/2000 | Bailey |
| 6,151,745 A | 11/2000 | Roberts et al. |
| 6,151,746 A | 11/2000 | Lewis |
| 6,168,434 B1 | 1/2001 | Bohm-Van Diggelen |
| 6,176,631 B1 | 1/2001 | Gueret |
| 6,178,582 B1 | 1/2001 | Halm |
| 6,182,323 B1 | 2/2001 | Bahten |
| 6,182,365 B1 | 2/2001 | Tseng et al. |
| 6,185,779 B1 | 2/2001 | Kramer |
| 6,190,367 B1 | 2/2001 | Hall |
| 6,192,544 B1 | 2/2001 | Persidsky et al. |
| 6,219,874 B1 | 4/2001 | Van Gelder et al. |
| 6,234,798 B1 | 5/2001 | Beals et al. |
| 6,237,178 B1 | 5/2001 | Krammer et al. |
| 6,240,590 B1 | 6/2001 | Nesbit |
| 6,245,032 B1 | 6/2001 | Sauer et al. |
| 6,253,404 B1 | 7/2001 | Boland et al. |
| 6,253,405 B1 | 7/2001 | Gutelius et al. |
| 6,254,390 B1 | 7/2001 | Wagner |
| 6,272,713 B1 | 8/2001 | Lotwin |
| 6,273,719 B1 | 8/2001 | Whitman |
| 6,276,019 B1 | 8/2001 | Leversby et al. |
| 6,276,020 B1 | 8/2001 | Leversby et al. |
| 6,308,367 B1 | 10/2001 | Beals et al. |
| 6,311,358 B1 | 11/2001 | Soetewey et al. |
| 6,311,360 B1 | 11/2001 | Lanvers |
| 6,314,605 B1 | 11/2001 | Solanki et al. |
| 6,314,606 B1 | 11/2001 | Hohlbein |
| 6,319,332 B1 | 11/2001 | Gavney, Jr. et al. |
| 6,325,626 B1 | 12/2001 | Blass |
| 6,327,735 B1 | 12/2001 | Kramer |
| 6,334,231 B2 | 1/2002 | Safieh |
| 6,347,425 B1 | 2/2002 | Fattori et al. |
| 6,353,958 B2 | 3/2002 | Weihrauch |
| 6,357,074 B1 | 3/2002 | Weihrauch |
| 6,374,448 B2 * | 4/2002 | Seifert ............. 15/110 |
| 6,374,449 B1 | 4/2002 | Jolly |
| 6,389,634 B1 | 5/2002 | Devlin et al. |
| 6,408,473 B1 | 6/2002 | Kessler |
| 6,408,476 B1 | 6/2002 | Cann |
| 6,442,786 B2 | 9/2002 | Halm et al. |
| 6,442,787 B2 | 9/2002 | Hohlbein |
| 6,446,295 B1 | 9/2002 | Calabrese |
| 6,463,618 B1 | 10/2002 | Zimmer |
| 6,463,619 B2 | 10/2002 | Gavney, Jr. |
| 6,490,747 B1 | 12/2002 | Metwally |
| 6,502,272 B1 | 1/2003 | Fox et al. |
| 6,505,373 B2 | 1/2003 | Van Gelder et al. |
| 6,510,575 B2 | 1/2003 | Calabrese |
| 6,513,182 B1 | 2/2003 | Calabrese et al. |
| 6,514,445 B1 | 2/2003 | Cann et al. |
| 6,536,068 B1 | 3/2003 | Yang et al. |
| 6,546,583 B1 | 4/2003 | Rhrig |
| 6,547,750 B2 | 4/2003 | Huang |
| 6,553,604 B1 | 4/2003 | Braun et al. |
| 6,554,614 B1 | 4/2003 | Dubbe et al. |
| 6,568,020 B1 | 5/2003 | Hosokawa |
| D476,157 S | 6/2003 | Gatzemeyer et al. |
| 6,571,417 B1 * | 6/2003 | Gavney et al. ............. 15/117 |
| 6,599,048 B2 | 7/2003 | Kuo |
| 6,612,770 B2 | 9/2003 | Aoyama |
| 6,618,893 B1 | 9/2003 | Wang |
| 6,654,979 B2 | 12/2003 | Calabrese |
| 6,658,688 B2 | 12/2003 | Gavney |
| 6,665,901 B2 | 12/2003 | Driesen et al. |
| 6,668,416 B1 | 12/2003 | Georgi et al. |
| 6,671,919 B2 | 1/2004 | Davis |
| 6,675,428 B2 | 1/2004 | Halm |
| 6,687,940 B1 | 2/2004 | Gross et al. |
| 6,694,559 B1 | 2/2004 | Sloan |
| 6,708,364 B1 | 3/2004 | Huber |
| 6,721,987 B2 | 4/2004 | McDevitt et al. |
| 6,725,493 B2 | 4/2004 | Calabrese et al. |
| RE38,521 E | 5/2004 | Halm |
| 6,743,822 B2 | 6/2004 | Styczynski et al. |
| 6,766,548 B1 | 7/2004 | Lukas et al. |
| 6,772,465 B2 | 8/2004 | Mehta |
| 6,779,851 B2 | 8/2004 | Bouchiere |
| 6,792,642 B2 | 9/2004 | Wagstaff |
| 6,793,434 B1 | 9/2004 | Olson |
| 6,802,097 B2 | 10/2004 | Hfliger et al. |
| 6,805,557 B2 | 10/2004 | Davies |
| 6,807,703 B2 | 10/2004 | Van Gelder et al. |
| 6,808,068 B2 | 10/2004 | Abada |
| 6,810,551 B1 | 11/2004 | Weihrauch |
| 6,813,793 B2 | 11/2004 | Eliav |
| 6,813,794 B2 | 11/2004 | Weng |
| 6,817,054 B2 | 11/2004 | Moskovich et al. |
| 6,823,554 B1 | 11/2004 | Braun et al. |
| 6,826,797 B1 | 12/2004 | Chenvainu et al. |
| 6,832,819 B1 | 12/2004 | Weihrauch |
| D501,605 S | 2/2005 | Brown, Jr. et al. |
| 6,851,150 B2 | 2/2005 | Chiang |
| 6,851,431 B2 | 2/2005 | Mayeri |
| 6,859,968 B2 | 3/2005 | Miller et al. |
| 6,862,771 B1 | 3/2005 | Muller |
| 6,865,767 B1 | 3/2005 | Gavney, Jr. |
| 6,871,374 B2 | 3/2005 | Brezler et al. |
| 6,874,194 B1 | 4/2005 | Harris |
| 6,883,200 B1 | 4/2005 | Euler |
| 6,886,207 B1 | 5/2005 | Solanki |
| 6,886,208 B1 | 5/2005 | Kemp et al. |
| 6,889,401 B2 | 5/2005 | Fattori et al. |
| 6,892,412 B2 | 5/2005 | Gatzemeyer et al. |
| 6,895,624 B2 | 5/2005 | Fischer et al. |
| 6,907,638 B2 | 6/2005 | Katz |
| 6,920,659 B2 | 7/2005 | Cacka et al. |
| 6,931,688 B2 | 8/2005 | Moskovich et al. |
| 6,932,216 B2 | 8/2005 | Blaustein et al. |
| 6,938,293 B2 | 9/2005 | Eliav et al. |
| 6,938,294 B2 | 9/2005 | Fattori et al. |
| 6,944,901 B2 | 9/2005 | Gatzemeyer et al. |
| 6,944,903 B2 | 9/2005 | Gavney |
| 6,948,209 B2 | 9/2005 | Chan |
| 6,952,856 B2 | 10/2005 | Kaizuka |
| 6,954,961 B2 | 10/2005 | Ferber et al. |
| 6,957,467 B2 | 10/2005 | Cabedo-Deslierres et al. |
| 6,957,469 B2 | 10/2005 | Davies |
| 6,964,603 B2 | 11/2005 | Fischer et al. |
| 6,966,093 B2 | 11/2005 | Eliav et al. |
| 6,968,590 B2 | 11/2005 | Ponzini |
| 6,983,507 B2 | 1/2006 | McDougall |
| 6,988,292 B1 | 1/2006 | Wang |
| 6,988,777 B2 | 1/2006 | Pfenniger et al. |
| 6,990,706 B2 | 1/2006 | Broecker et al. |
| 6,993,804 B1 | 2/2006 | Braun et al. |
| 6,996,870 B2 | 2/2006 | Hohlbein |
| 7,003,839 B2 | 2/2006 | Hafliger et al. |
| 7,007,332 B2 | 3/2006 | Hohlbein |
| 7,007,335 B2 | 3/2006 | Doat |
| 7,013,522 B2 | 3/2006 | Kumagai |
| 7,020,925 B1 | 4/2006 | Gitelis |
| 7,020,928 B2 | 4/2006 | Hohlbein |
| 7,024,720 B2 | 4/2006 | Moskovich et al. |
| 7,036,179 B2 | 5/2006 | Weihrauch |
| 7,039,984 B1 | 5/2006 | Watanabe et al. |
| 7,047,589 B2 | 5/2006 | Gavney, Jr. |
| 7,047,591 B2 | 5/2006 | Hohlbein |
| 7,051,394 B2 | 5/2006 | Gavney, Jr. |
| 7,055,205 B2 | 6/2006 | Aoyama |
| 7,069,615 B2 | 7/2006 | Gavney, Jr. |
| 7,073,255 B1 | 7/2006 | Swanson et al. |
| 7,086,116 B2 | 8/2006 | Broecker et al. |
| 7,089,621 B2 | 8/2006 | Hohlbein |
| 7,111,350 B2 | 9/2006 | Blackman et al. |
| 7,117,555 B2 | 10/2006 | Fattori et al. |
| 7,137,163 B2 | 11/2006 | Gatzemeyer et al. |

| | | |
|---|---|---|
| 7,140,058 B2 | 11/2006 | Gatzemeyer et al. |
| 7,143,462 B2 | 12/2006 | Hohlbein |
| 7,160,508 B2 | 1/2007 | Lee |
| 7,162,767 B2 | 1/2007 | Pfenniger et al. |
| 7,174,596 B2 * | 2/2007 | Fischer et al. .................. 15/110 |
| 7,181,799 B2 | 2/2007 | Gavney et al. |
| 7,185,383 B2 | 3/2007 | Gatzemeyer et al. |
| 7,210,184 B2 | 5/2007 | Eliva et al. |
| 7,226,555 B2 | 6/2007 | Weihrauch |
| 7,228,583 B2 | 6/2007 | Chan et al. |
| 7,322,067 B2 | 1/2008 | Hohlbein |
| 7,392,562 B2 | 7/2008 | Boland et al. |
| 7,546,658 B2 | 6/2009 | Koeth et al. |
| 7,562,411 B2 | 7/2009 | Gavney, Jr. |
| 7,814,603 B2 | 10/2010 | Gavney, Jr. |
| 2001/0008032 A1 | 7/2001 | Llewellyn-Jones et al. |
| 2001/0023516 A1 * | 9/2001 | Driesen et al. ................ 15/167.1 |
| 2001/0039689 A1 | 11/2001 | Gavney, Jr. |
| 2002/0056197 A1 | 5/2002 | Johnson |
| 2002/0059685 A1 | 5/2002 | Paffrath |
| 2002/0084550 A1 | 7/2002 | Roberts et al. |
| 2002/0100134 A1 | 8/2002 | Dunn et al. |
| 2002/0138931 A1 | 10/2002 | Davies |
| 2002/0152564 A1 | 10/2002 | Blaustein et al. |
| 2002/0157202 A1 | 10/2002 | Hartel |
| 2003/0009837 A1 | 1/2003 | Cann |
| 2003/0014826 A1 | 1/2003 | Touzani |
| 2003/0019060 A1 | 1/2003 | Gavney, Jr. |
| 2003/0033680 A1 | 2/2003 | Davies et al. |
| 2003/0033682 A1 | 2/2003 | Davies et al. |
| 2003/0036561 A1 | 2/2003 | Styczynski et al. |
| 2003/0041402 A1 | 3/2003 | Stein et al. |
| 2003/0077107 A1 | 4/2003 | Kuo |
| 2003/0140437 A1 | 7/2003 | Eliav |
| 2003/0140440 A1 | 7/2003 | Gavney, Jr. |
| 2003/0140442 A1 | 7/2003 | Aoyama |
| 2003/0154567 A1 | 8/2003 | Drossler et al. |
| 2003/0159224 A1 | 8/2003 | Fischer et al. |
| 2003/0163882 A1 | 9/2003 | Blaustein et al. |
| 2003/0182746 A1 | 10/2003 | Fattori et al. |
| 2003/0196283 A1 | 10/2003 | Eliav et al. |
| 2003/0208870 A1 | 11/2003 | Jimenez |
| 2003/0213075 A1 | 11/2003 | Hui et al. |
| 2003/0226223 A1 | 12/2003 | Chan |
| 2003/0229959 A1 | 12/2003 | Gavney, Jr. et al. |
| 2004/0006837 A1 | 1/2004 | Cann |
| 2004/0010870 A1 | 1/2004 | McNair |
| 2004/0025272 A1 | 2/2004 | Stvartak et al. |
| 2004/0025274 A1 | 2/2004 | Moskovich et al. |
| 2004/0025275 A1 | 2/2004 | Moskovich et al. |
| 2004/0060135 A1 * | 4/2004 | Gatzemeyer et al. .......... 15/22.1 |
| 2004/0060136 A1 | 4/2004 | Gatzemeyer et al. |
| 2004/0060137 A1 | 4/2004 | Eliav |
| 2004/0068811 A1 | 4/2004 | Fulop et al. |
| 2004/0074034 A1 | 4/2004 | Russell |
| 2004/0074035 A1 | 4/2004 | Huang |
| 2004/0087882 A1 | 5/2004 | Roberts et al. |
| 2004/0088807 A1 | 5/2004 | Blaustein et al. |
| 2004/0088812 A1 | 5/2004 | Weihrauch |
| 2004/0134007 A1 | 7/2004 | Davies |
| 2004/0154112 A1 | 8/2004 | Braun |
| 2004/0154118 A1 | 8/2004 | Bohn |
| 2004/0168271 A1 | 9/2004 | McDougall |
| 2004/0177462 A1 | 9/2004 | Brown et al. |
| 2004/0187887 A1 | 9/2004 | Beckmann |
| 2004/0200016 A1 | 10/2004 | Chan et al. |
| 2004/0200748 A1 | 10/2004 | Klassen et al. |
| 2004/0211018 A1 | 10/2004 | Canton et al. |
| 2004/0231082 A1 | 11/2004 | Gavney, Jr. |
| 2004/0237226 A1 | 12/2004 | Hohlbein et al. |
| 2004/0255416 A1 | 12/2004 | Hohlbein |
| 2004/0255427 A1 | 12/2004 | Gavney, Jr. |
| 2004/0261207 A1 | 12/2004 | Gavney, Jr. |
| 2005/0000043 A1 | 1/2005 | Chan et al. |
| 2005/0011024 A1 | 1/2005 | Ping et al. |
| 2005/0015904 A1 | 1/2005 | Gavney, Jr. |
| 2005/0015907 A1 | 1/2005 | Georgi et al. |
| 2005/0022322 A1 | 2/2005 | Jimenez et al. |
| 2005/0039279 A1 | 2/2005 | Koeth et al. |
| 2005/0049155 A1 | 3/2005 | Gavney, Jr. |
| 2005/0060826 A1 | 3/2005 | Gavney, Jr. |
| 2005/0066456 A1 | 3/2005 | Gavney, Jr. |
| 2005/0066462 A1 | 3/2005 | Moskovich et al. |
| 2005/0069372 A1 | 3/2005 | Hohlbein et al. |
| 2005/0071939 A1 | 4/2005 | Wong |
| 2005/0091767 A1 | 5/2005 | Jimenez et al. |
| 2005/0091769 A1 | 5/2005 | Jimenez et al. |
| 2005/0091773 A1 | 5/2005 | Gavney, Jr. et al. |
| 2005/0097693 A1 | 5/2005 | Bransky et al. |
| 2005/0107017 A1 | 5/2005 | Fiorotti |
| 2005/0138743 A1 | 6/2005 | Huber et al. |
| 2005/0138744 A1 | 6/2005 | Hohlbein |
| 2005/0138745 A1 | 6/2005 | Huang |
| 2005/0155172 A1 | 7/2005 | Gavney, Jr. |
| 2005/0160541 A1 | 7/2005 | Goldfine |
| 2005/0166341 A1 | 8/2005 | Solanki |
| 2005/0188487 A1 | 9/2005 | Moskovich et al. |
| 2005/0188488 A1 | 9/2005 | Moskovich et al. |
| 2005/0188489 A1 | 9/2005 | Hohlbein |
| 2005/0193512 A1 | 9/2005 | Moskovich et al. |
| 2005/0198753 A1 | 9/2005 | Berde et al. |
| 2005/0198757 A1 | 9/2005 | Gavney, Jr. et al. |
| 2005/0210612 A1 | 9/2005 | Hohlbein et al. |
| 2005/0210613 A1 | 9/2005 | Wagstaff |
| 2005/0229339 A1 | 10/2005 | Gavney, Jr. et al. |
| 2005/0235439 A1 | 10/2005 | Braun et al. |
| 2005/0241091 A1 | 11/2005 | Foster et al. |
| 2005/0273952 A1 | 12/2005 | Chan et al. |
| 2005/0273954 A1 | 12/2005 | Gavney, Jr. |
| 2005/0273961 A1 | 12/2005 | Moskovich et al. |
| 2005/0278883 A1 | 12/2005 | Hohlbein |
| 2006/0000036 A1 | 1/2006 | Eliav et al. |
| 2006/0010623 A1 | 1/2006 | Crossman et al. |
| 2006/0010628 A1 | 1/2006 | Moskovich |
| 2006/0010631 A1 | 1/2006 | Geiberger |
| 2006/0021170 A1 | 2/2006 | Gavney, Jr. |
| 2006/0026784 A1 | 2/2006 | Moskovich et al. |
| 2006/0037160 A1 | 2/2006 | Kayser |
| 2006/0059642 A1 | 3/2006 | Solanki |
| 2006/0064827 A1 | 3/2006 | Chan |
| 2006/0064833 A1 | 3/2006 | Jacobs |
| 2006/0075588 A1 | 4/2006 | Amador |
| 2006/0085932 A1 | 4/2006 | Santos |
| 2006/0107474 A1 | 5/2006 | McDougall |
| 2006/0117506 A1 | 6/2006 | Gavney, Jr. et al. |
| 2006/0117508 A1 | 6/2006 | Hohlbein |
| 2006/0230563 A1 | 10/2006 | Gavney, Jr. |
| 2006/0236477 A1 | 10/2006 | Gavney, Jr. |
| 2007/0033755 A1 | 2/2007 | Gavney, Jr. |
| 2007/0074361 A1 | 4/2007 | Gavney, Jr. |
| 2007/0271717 A1 | 11/2007 | Clos et al. |
| 2008/0201885 A1 | 8/2008 | Moskovich |
| 2009/0282628 A1 | 11/2009 | Braun |

FOREIGN PATENT DOCUMENTS

| | | |
|---|---|---|
| DE | 1992022 | 5/1968 |
| DE | 2526893 | 12/1976 |
| DE | 4201873 | 5/1993 |
| DE | 4303431 | 8/1993 |
| DE | 19717868 | 10/1998 |
| DE | 10122987 | 11/2002 |
| DE | 20111428 | 1/2003 |
| DE | 10164336 | 7/2003 |
| EP | 360766 | 3/1990 |
| EP | 1004282 | 5/2000 |
| EP | 0918477 | 3/2003 |
| EP | 1584263 | 10/2005 |
| EP | 1661487 | 5/2006 |
| EP | 1700537 | 9/2006 |
| FR | 936529 | 7/1948 |
| FR | 2636818 | 3/1990 |
| GB | 2040161 | 1/1979 |
| JP | 26-008198 | 7/1949 |
| JP | 1971013226 | 5/1971 |
| JP | 51-07676 U | 6/1976 |
| JP | 197810671 | 1/1978 |
| JP | 198099210 | 7/1980 |
| JP | 1989500490 | 2/1989 |

| | | |
|---|---|---|
| JP | 1989181807 | 6/1989 |
| JP | 1990089925 | 7/1990 |
| JP | 19979019323 | 1/1997 |
| JP | 1997502118 | 3/1997 |
| JP | 1998262733 | 10/1998 |
| JP | 11332651 | 12/1999 |
| JP | 2000300342 | 10/2000 |
| JP | 2001504024 | 2/2001 |
| JP | 2001070043 | 3/2001 |
| JP | 2001178540 | 7/2001 |
| JP | 2001275751 | 10/2001 |
| JP | 2001286343 | 10/2001 |
| JP | 2002010832 | 1/2002 |
| JP | 2002500903 | 1/2002 |
| JP | 2002034657 | 2/2002 |
| JP | 2002514946 | 5/2002 |
| JP | 2002199938 | 7/2002 |
| JP | 2003153741 | 5/2003 |
| JP | 2003225122 | 8/2003 |
| JP | 2003523788 | 8/2003 |
| JP | 2004538029 | 12/2004 |
| JP | 2005305116 | 11/2005 |
| WO | 8700032 | 1/1987 |
| WO | 8707500 | 12/1987 |
| WO | 9609781 | 4/1996 |
| WO | 9615696 | 5/1996 |
| WO | 9716995 | 5/1997 |
| WO | 9818364 | 5/1998 |
| WO | 0049911 | 8/2000 |
| WO | 0064307 | 11/2000 |
| WO | 0074522 | 12/2000 |
| WO | 0121036 | 3/2001 |
| WO | WO 01/26505 | 4/2001 |
| WO | 0211583 | 2/2002 |
| WO | 03015575 | 2/2003 |
| WO | 03030680 | 4/2003 |
| WO | WO03043459 | 5/2003 |
| WO | 03055351 | 7/2003 |
| WO | 2004014181 | 2/2004 |
| WO | 2004014182 | 2/2004 |
| WO | 2004014183 | 2/2004 |
| WO | 2004016188 | 2/2004 |
| WO | 2004026077 | 4/2004 |
| WO | 2004028235 | 4/2004 |
| WO | 2004062519 | 7/2004 |
| WO | 2004062573 | 7/2004 |
| WO | 2005084486 | 9/2005 |
| WO | 2006005624 | 1/2006 |
| WO | 2006012974 | 2/2006 |

OTHER PUBLICATIONS

Examiner's Answer for U.S. Appl. No. 10/364,148 dated Jun. 3, 2008.
Office Action for U.S. Appl. No. 10/364,148 dated Dec. 21, 2007.
Office Action for U.S. Appl. No. 10/364,148 dated Jul. 6, 2007.
Advisory Action for U.S. Appl. No. 10/364,148 dated May 7, 2007.
Office Action for U.S. Appl. No. 10/364,148 dated Dec. 21, 2006.
Office Action for U.S. Appl. No. 10/364,148 dated May 12, 2006.
Office Action for U.S. Appl. No. 10/364,148 dated Nov. 14, 2005.
Office Action for U.S. Appl. No. 10/364,148 dated May 5, 2005.
Office Action for U.S. Appl. No. 10/364,148 dated Dec. 16, 2004.
Office Action for U.S. Appl. No. 10/364,148 dated Jul. 14, 2004.
Office Action for U.S. Appl. No. 11/569,789 dated Jun. 11, 2010.
Office Action for U.S. Appl. No. 11/569,789 dated Nov. 24, 2009.

* cited by examiner

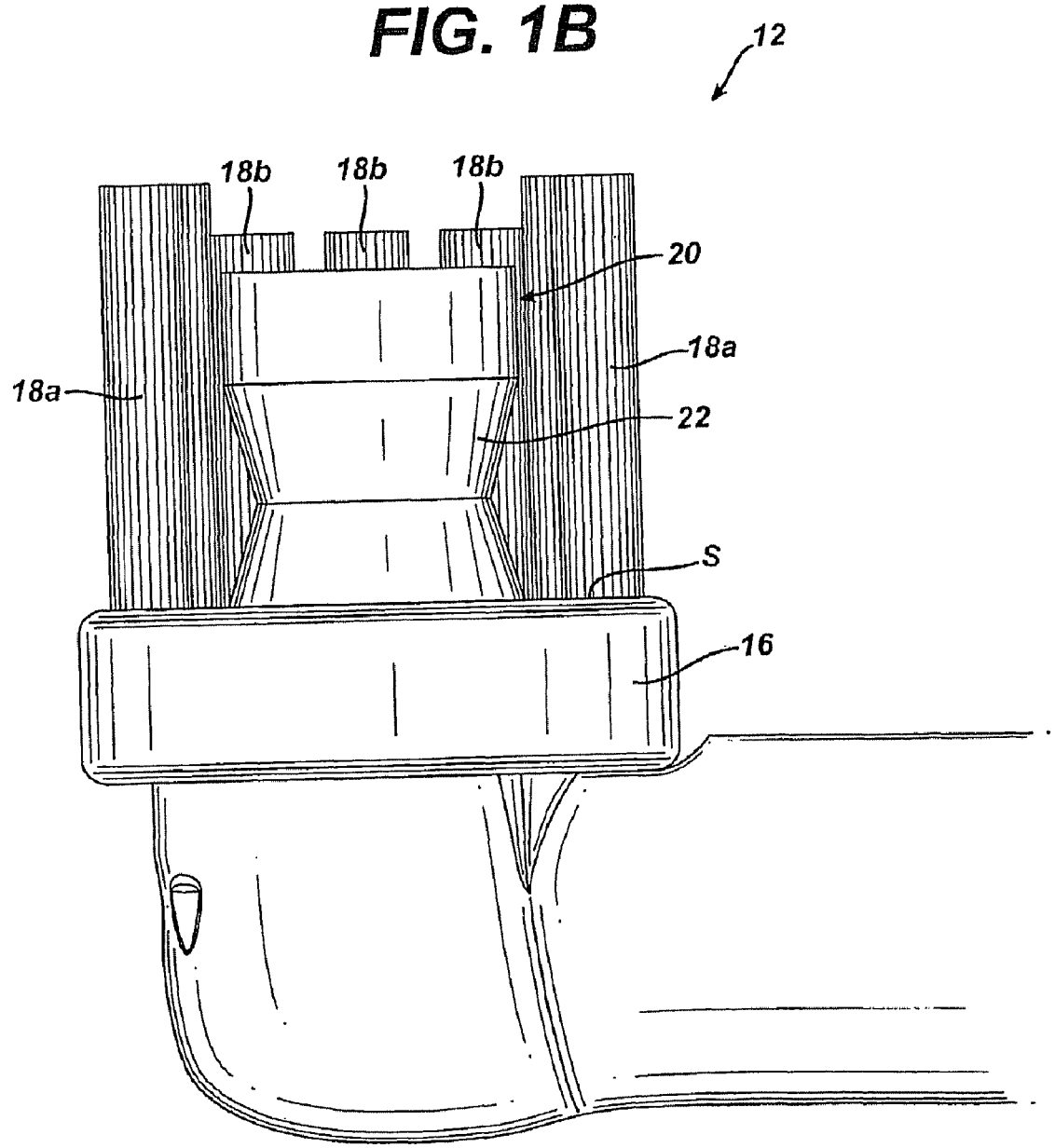

FIG. 2
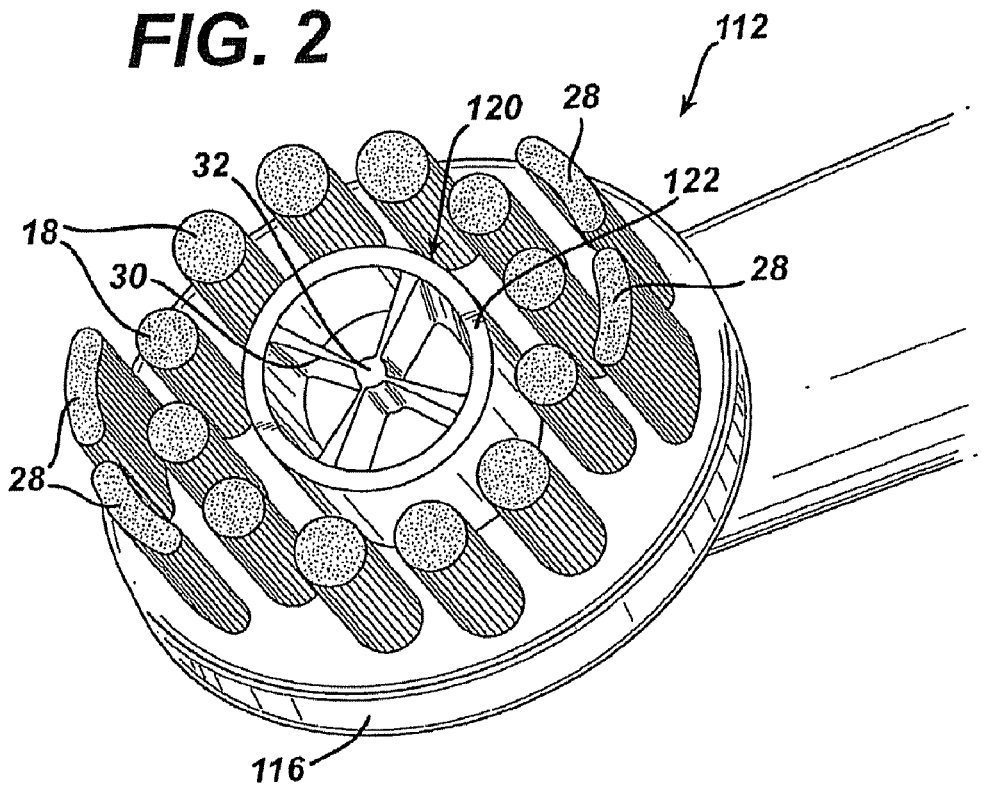
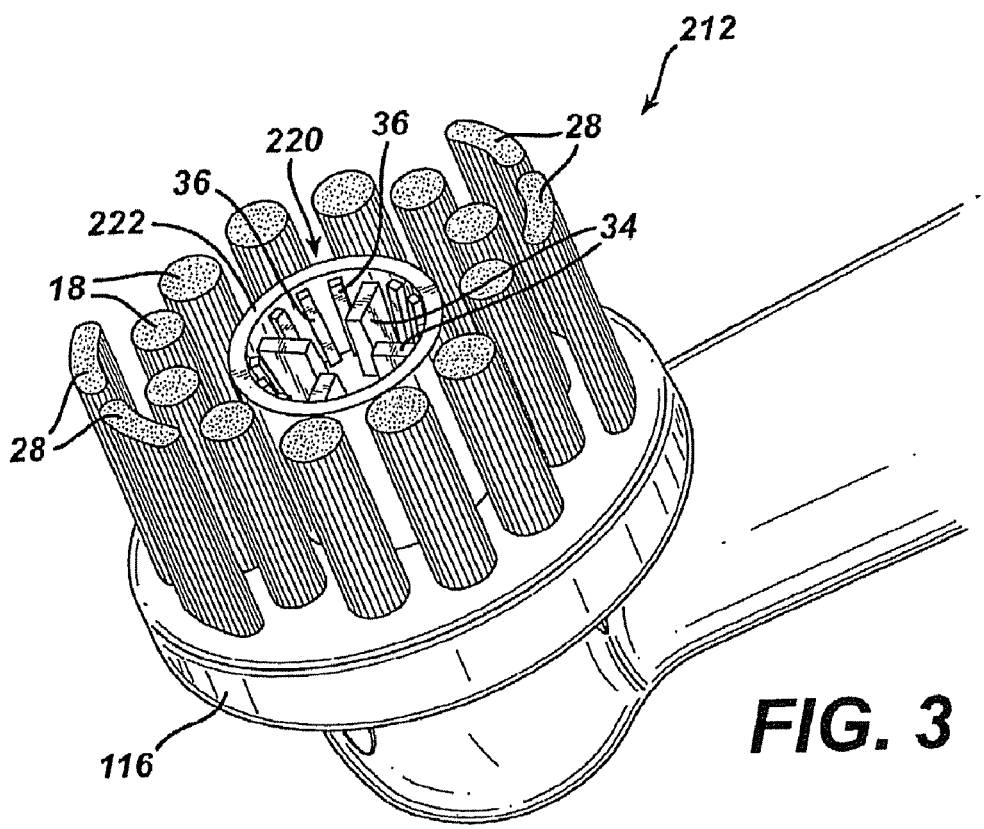
FIG. 3

TOOTHBRUSHES

CROSS REFERENCE TO RELATED APPLICATIONS

This application is a continuation of U.S. Non-Provisional application Ser. No. 10/364,148 filed on Feb. 11, 2003, which is entitled TOOTHBRUSHES and which is incorporated herein by reference in its entirety.

TECHNICAL FIELD

This invention relates to toothbrushes, and more particularly to power toothbrushes.

BACKGROUND

Power toothbrushes are well known and have been on the market for years. In typical power toothbrushes, tufts of bristles on the brush head extend generally perpendicularly from the top surface of the head. The head is oscillated, rotated and/or translated in order to provide enhanced tooth cleaning capability.

SUMMARY

In one aspect, the invention features a toothbrush head that includes a support member, a resilient member extending from the support member, and a plurality of bristles or tufts of bristles extending from the support member and at least partially surrounding the resilient member. By "resilient member" we mean a unitary structure formed of a resilient material such as an elastomer or foam, the resilient member having a perimeter, when the resilient member is viewed from above (e.g., looking down the long axis of the bristles, if the bristles and resilient member are disposed perpendicular to the support member), which circumscribes an area greater than the surface area of the resilient member that will initially contact the teeth of a user of the toothbrush. By "initially contact the teeth," we mean the surface area that will contact the teeth and/or gums prior to any significant deformation of the resilient member resulting from the application of pressure against the teeth, i.e., the area that would contact the teeth if the toothbrush were lightly touched to the teeth with the power turned off. By "unitary structure," we mean that, if the resilient member includes a plurality of elements, such as fins, protrusions or lammelae, the elements are integrally joined to form a single structure that is mounted on the separate support member.

In one aspect, the resilient member may be cup-shaped.

The term "cup-shaped," as used herein, refers to a shape that is generally elliptical, oval, ovoid, or circular in cross-section and that defines a central open area. The walls of the cup-shaped member may be continuous or discontinuous and may define a cylinder, cone, frustoconical shape, or other desired shape. The bottom of the central open area may be flat, concave, or any other desired shape.

In another aspect, the resilient member may be fan-shaped.

The term "fan-shaped," as used herein, refers to a shape that is generally comprised of a central hub region and at least two protrusions, e.g., ribs, fins, or other types of protrusions, that extend substantially radially from the central hub region. The protrusions may form a helix, spiral, screw, or other pattern. The central hub region may be solid, hollow, or cup-shaped, and may be, for example, generally elliptical, oval, ovoid, or circular in cross-section.

In a third aspect, the resilient member is "textured."

The term "textured," as used herein, refers to a structure that has a macroscopic surface texture. For example, the textured member may be composed of a cluster of ribs, fins, columns, or other protrusions, or a combination of ribs, fins, columns, or other protrusions, that together form a unitary structure. As other examples, the texture can be imparted to the member by a manufacturing process such as injection molding, by embedding particles in the surface of the member, or by selecting a material for the member that inherently has a surface texture, e.g., an open cell foam.

Some implementations include one or more of the following features.

The toothbrush head is configured for use on a power toothbrush. The cup-shaped, fan-shaped or textured member comprises a resilient material.

The cup-shaped member defines an open central area having a depth of from about 2 to 5 mm. The cup-shaped member includes a side wall that is substantially continuous. The cup-shaped member includes a plurality of segments that define a discontinuous side wall. The cup-shaped member includes a generally cylindrical, conical or frustoconical side wall.

The toothbrush head further includes a plurality of fin members extending inwardly from an inner surface of the cup-shaped member. The fins have different lengths, heights, and/or thicknesses. At least some of the fin members converge to intersect at a central hub. The central hub has a shape selected from the group consisting of cones, inverted cones, cups and cylinders. The converging fin members increase in height with increasing radial distance from the central hub. The cup-shaped member includes a wavy edge.

The toothbrush head further includes one or more inner cup-shaped members disposed concentrically within an open area defined by the cup-shaped member. The cup-shaped member and inner cup-shaped members are comprised of segments that define discontinuous outer walls of the cup-shaped members.

At least some of the tufts have different heights. The height of the bristle tufts is greater than the height of the cup-shaped member.

The fan-shaped member includes a plurality of protrusions extending radially from a central hub. The central hub is generally cylindrical or conical.

The textured member includes a plurality of lammelae extending from a common base. The textured member includes a molded element having an integrally molded surface texture. The textured member comprises a resilient member formed of a material having a macroscopic surface texture.

The invention also features methods of using and making the toothbrush heads described above.

In some implementations, the toothbrush head provides gum massaging and stimulation in addition to cleaning. The cup-shaped member may help position the toothbrush head on each individual tooth during brushing. This positioning of the head may in turn assist the user in obtaining a proper tooth-to-tooth brushing technique, rather than using a scrubbing motion. This seating action also helps to position the bristles surrounding the cup-shaped member to more effectively access areas between the teeth and along the gumline. In addition, the cup-shaped member may help hold the toothpaste against the teeth during brushing. As a result, tooth brushing may be less messy, and the toothbrush head may be able to hold more toothpaste. Also, toothpaste may tend to be concentrated against the tooth surface, which may in turn result in improved whitening, stain removal, and cleaning. The cup-shaped member may also enhance plaque removal.

In some embodiments, the cup-shaped member may be designed to enhance the foaming action of toothpaste.

In other implementations, the toothbrush head may provide enhanced surface cleaning by the motion of the fan-shaped or textured member, both of which provide a wiping action. The increased contact area of the member with the surface of the tooth may also provide enhanced whitening and stain removal.

Other features and advantages of the invention will be apparent from the description and drawings, and from the claims.

DESCRIPTION OF DRAWINGS

FIG. 1B is a side view of FIG. 1A.

FIG. 2 is a perspective view of a toothbrush head according to an alternative embodiment of the invention.

FIGS. 3-11 are perspective views of toothbrush heads according to various alternative embodiments of the invention, with the exception of FIG. 7A, which shows the toothbrush head shown in FIG. 7 with the front tufts of bristles removed to show the detail of the fan-shaped member.

DETAILED DESCRIPTION

Figure 1:
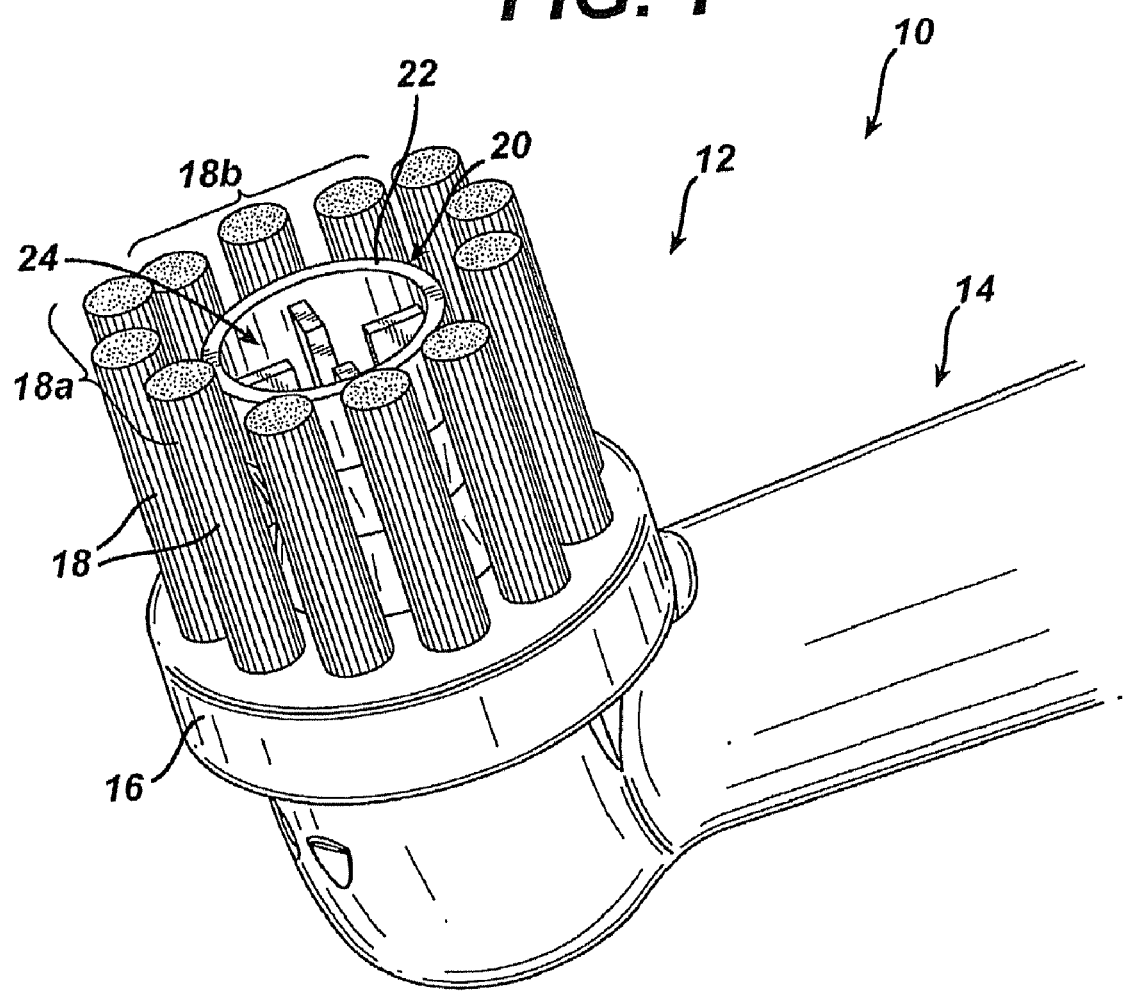
FIG. 1 is a perspective view of a portion of a power toothbrush, according to a first embodiment of the invention.

Referring to FIG. 1, a power toothbrush 10 includes a head 12 and a neck 14. As is well known to those skilled in the art, head 12 is oscillated during brushing. An electric motor (not shown) oscillates the head through gearing, linkages, cranks, and/or other drive mechanisms as is well known. Electrical power may be supplied to the motor by rechargeable or single use (disposable) batteries. Further details as to how the head is oscillated will not be provided, as this aspect of the brush is not the focus of the invention.

Head 12 includes a generally circular support member 16, and, extending from the support member 16, a plurality of bristle tufts 18. Although each tuft is shown as a solid mass in the drawings, the tufts are actually each made up of a great mass of individual plastic bristles. The bristles may be made of any desired polymer, e.g., nylon 6.12 or 6.10, and may have any desired diameter, e.g., 4-8 mil. The tufts are supported at their bases by the support member, and may be held in place by any desired tufting technique as is well known in the art, e.g., hot tufting or a stapling process. The tufts may also be mounted to move on the support member, as is well known in the toothbrush art.

Figure 1A:
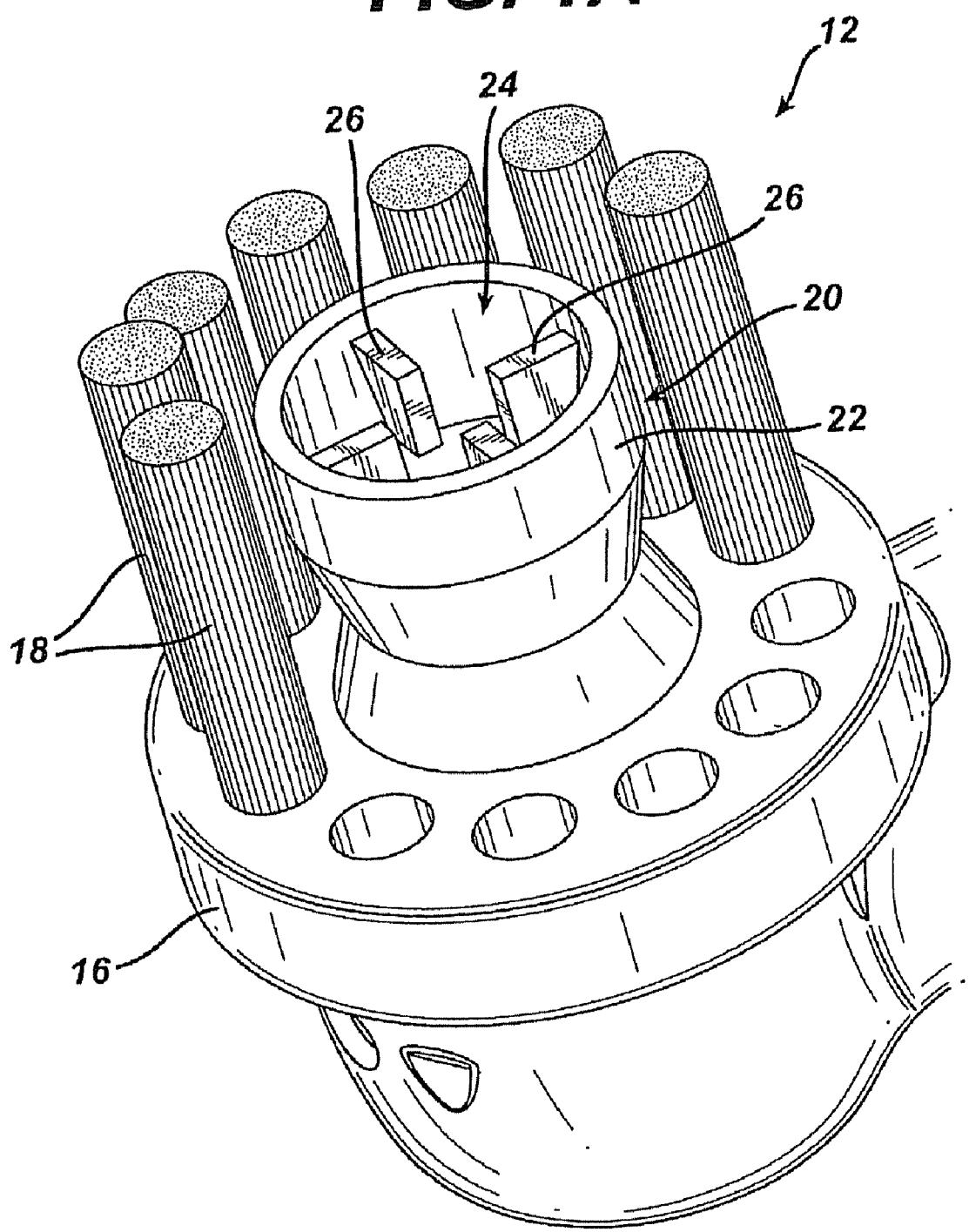
FIG. 1A is similar to FIG. 1, with the front tufts of bristles removed to show the detail of the cup-shaped member.

Head 12 further includes a cup-shaped member 20, which can be seen clearly in FIG. 1A, in which some of the bristle tufts have been omitted. Cup-shaped member 20 includes a side wall 22 that defines a central open area 24. Generally, the central open area 24 has a depth of from about 2 to 5 mm, measured from the highest point of the rim of the cup-shaped member to the lowest point of the central open area. Cup-shaped member 20 also includes a plurality of ribs 26 that extend inwardly into the open area 24. The cup-shaped member 20 is preferably formed of a resilient material such as an elastomer, e.g., a thermoplastic elastomer. The material hardness for such structures may range from 10 to 70 Shore A, with the preferred hardness selection depending on the design and dimensions of the cup-shaped member.

The cup-shaped member 20 may be fixedly mounted on the toothbrush head, or may be rotatably mounted, so that the cup-shaped member 20 can spin about its long axis while the toothbrush head is oscillated. The spinning motion may be driven by the same motor that oscillates the head, as would be understood by those skilled in the art. If the cup-shaped member is fixedly mounted, it may be mounted by any conventional technique, e.g., by screwing it in place or overmolding it onto the support member.

As shown in FIG. 1B, the height of bristle tufts 18 above the top surface S of support member 16 will generally be greater than the height of the cup-shaped member 20 from surface S. This height differential allows the head to contour around each tooth, enhancing the tooth-to-tooth indexing effect mentioned above.

There is also a height differential between the different bristle tufts. The end bristle tufts 18A, i.e., the tufts that are adjacent the long axis of the toothbrush neck 14 when the head 12 is at rest, are taller than the side tufts 18b. For example, the height of the cup-shaped member may be from about 5.5 to 10 mm, with the end tufts 18A being about 20 to 30% taller than the cup-shaped member, e.g., from about 6.6 to 13 mm in height, and the side tufts 18b being about 5 to 15% taller than the cup-shaped member, e.g., about 5.8 to 11.5 mm in height. Making the side tufts shorter than the end tufts allows the longer tufts to reach in between the teeth, while the shorter tufts clean along the gumline.

Toothbrush heads according to other embodiments are shown in FIGS. 2-10. In each of these embodiments, the support members 116 are generally elliptical, rather than circular as shown in FIG. 1. The elliptical shape provides more room for additional bristle tufts, and thus these toothbrush heads further include curved, elongated interdental tufts 28. In these embodiments, the cup-shaped member and bristle tufts are generally shorter than in the embodiment discussed above. In an elliptical head, the reduced height will tend to make the brush more comfortable and less "bulky" feeling in a user's mouth. As in the embodiment discussed above, the bristle tufts are generally taller than the cup-shaped member. As shown in FIG. 2A, the interdental tufts 28 are also taller than the cup-shaped member, e.g., by about 30 to 40%.

Each of the embodiments shown in FIGS. 2-7 includes a different type of cup-shaped member.

Figure 2A:
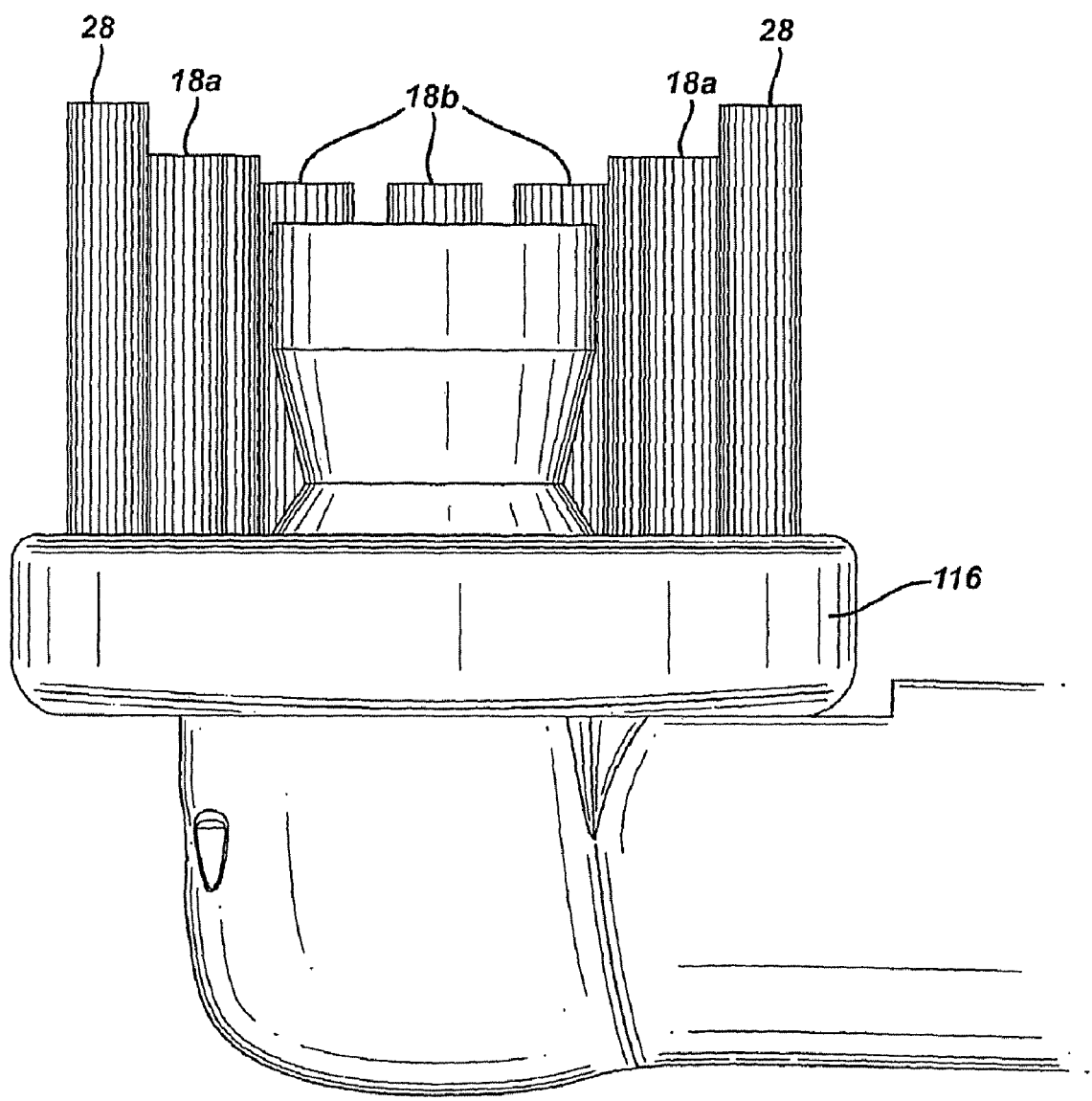
FIG. 2A is a side view of a toothbrush head similar to the one shown in FIG. 2 with the front tufts of bristles removed to show the detail of the cup-shaped member.
Figure 2B:
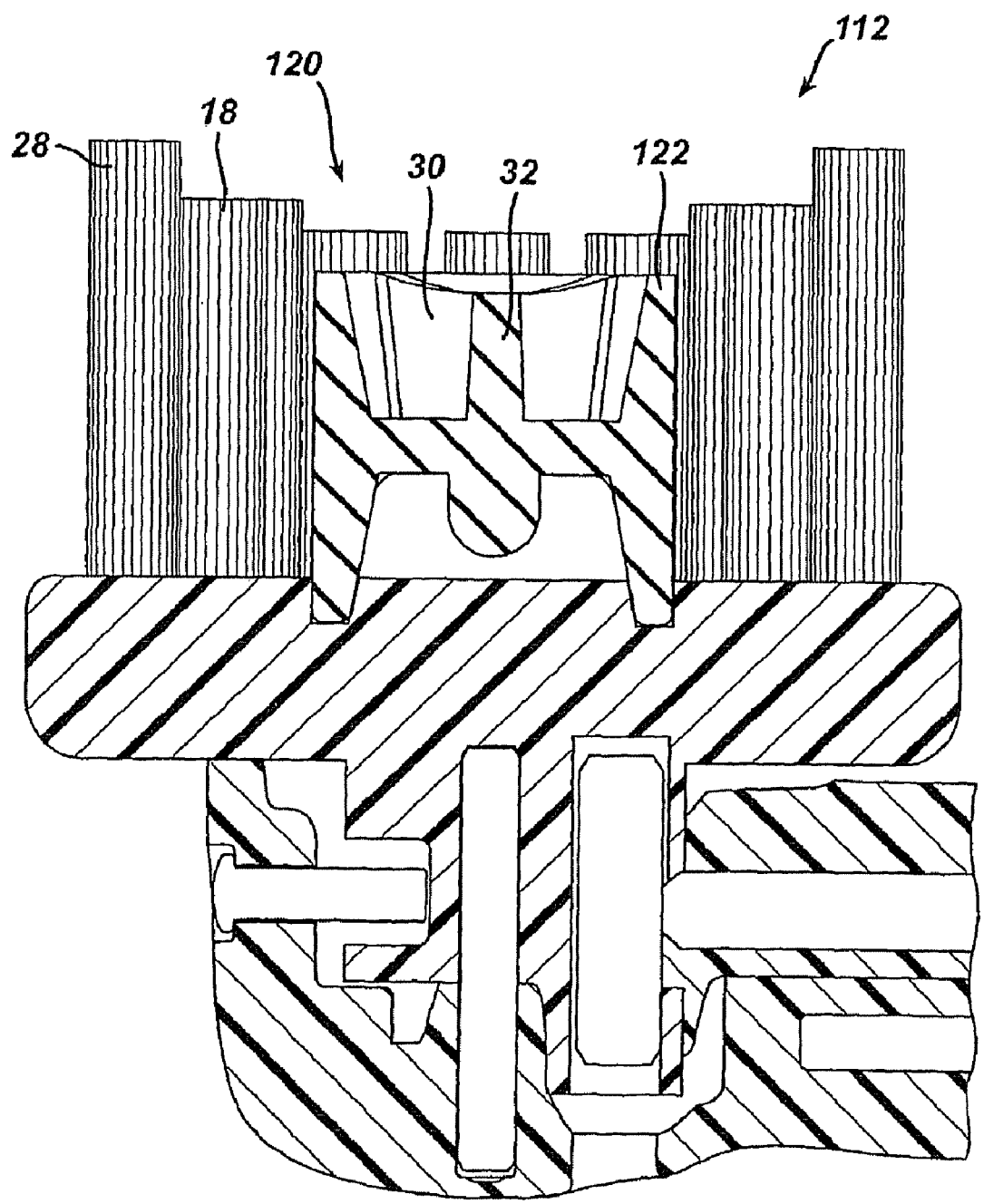
FIG. 2B is a cross-sectional view of the toothbrush head shown in FIG. 2, taken along the long axis of the toothbrush.

In head 112, shown in FIG. 2, cup shaped member 120 includes a side wall 122, and extending inwardly from the side wall, a plurality of ribs 30 that converge at a generally cylindrical central hub 32. In alternate embodiments (not shown) the central hub may be conical or cup-shaped. In this design, as shown in FIG. 2B, the ribs are at the same height as the cup at the outer perimeter, and decrease in height as they approach the center. This arrangement allows the ribs to act as "squeegees" to clean the tooth surface. The addition of the central hub adds strength to the total structure and the ribs. If this additional strength is not required for a particular design, the central hub may be omitted, and the ribs may simply intersect each other, or may stop short of intersecting. In head 212, shown in FIG. 3, cup-shaped member 220 includes a side wall 222 and, extending inwardly from the side wall, a plurality of larger ribs 34 and smaller ribs 36. The larger ribs are longer (i.e., extend further into the center), and may have a different thickness and/or height than the smaller ribs.

Figure 4:
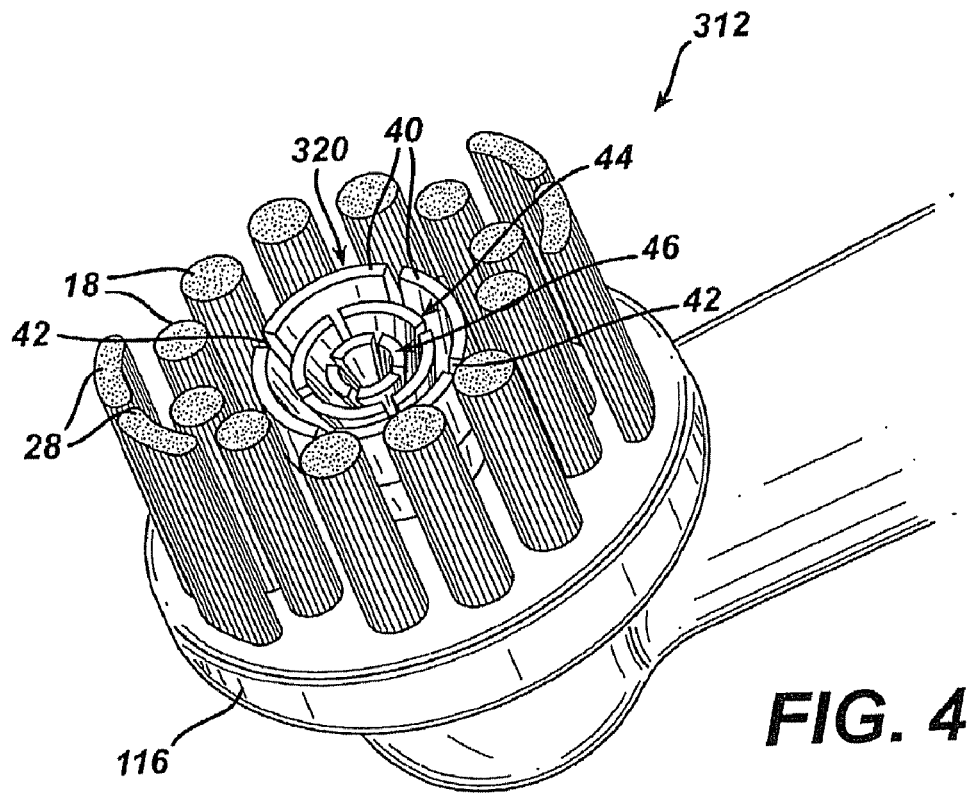
Figure 5:
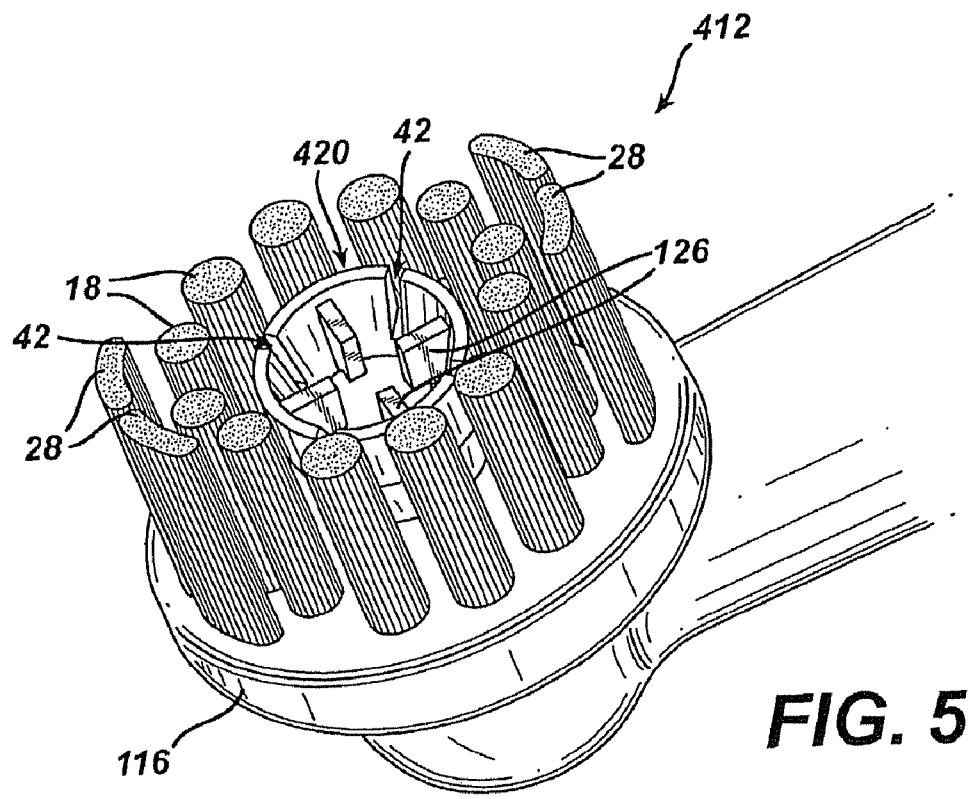

In the embodiments shown in FIGS. 4 and 5, the cup-shaped member is segmented, i.e., it has a discontinuous side wall that includes a plurality of arcuate segments. The segmented structure imparts flexibility to the cup-shaped member, and may allow the cup-shaped member to conform better to the tooth surface. As can be seen in FIG. 5, in these embodiments the segments are defined by grooves 42 that do not extend to the bottom of the cup-shaped member. As a result, the segments are connected to form a unitary structure.

In head 312, shown in FIG. 4, cup-shaped member 320 includes a segmented side wall that includes four arcuate segments 40 having grooves 42 therebetween. Within the open center area defined by the cup-shaped member 320 are disposed two concentrically arranged smaller inner cup-shaped members 44 and 46. These inner cup-shaped members have the same segmented structure as the outer cup-shaped member 320. The concentric members provide a large surface area for contact with the tooth surface, which may provide improved cleaning.

In head 412, shown in FIG. 5, cup-shaped member 420 again includes a segmented side wall comprised of four arcuate segments. In this embodiment, ribs 126 extend inwardly from the side wall, as in the embodiment shown in FIG. 1.

Figure 6:
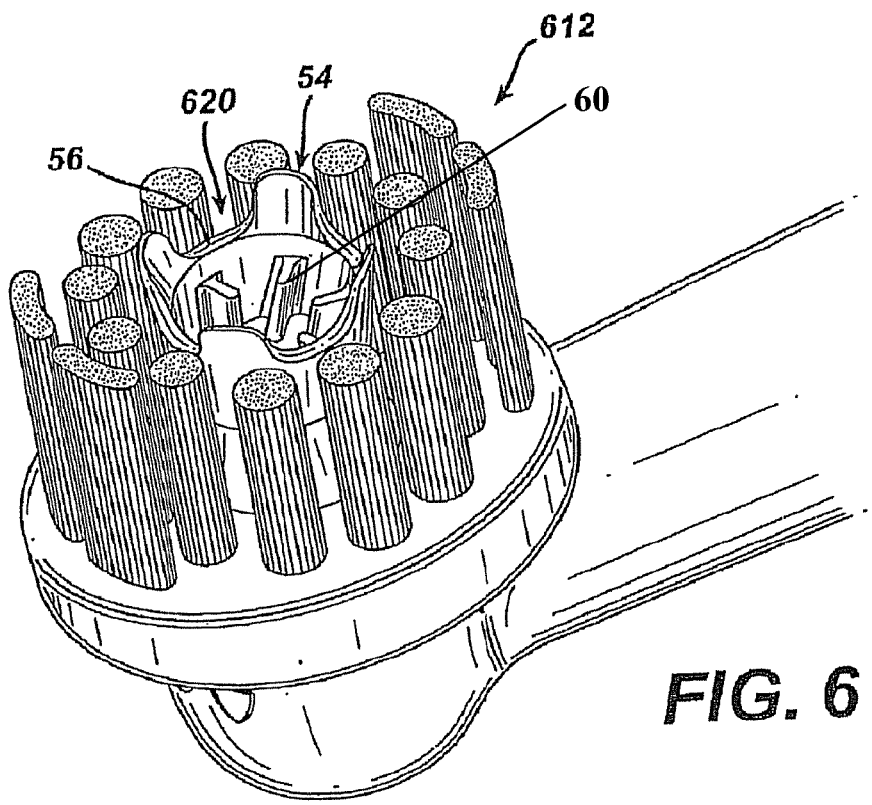

In the embodiment shown in FIG. 6, head 612 includes a cup-shaped member 620 that has a wavy fringe 54 extending above its upper edge 56. The wavy fringe is relatively soft and flexible, so that it will lay flat when pressed against the surface of the teeth. This may allow the fringe to slide under the gums and between the teeth, providing plaque removal and gum stimulation which may reduce gingivitis. Generally, the fringe has a thickness of about 0.15 to 0.25 mm, measured at its top edge, and about 0.4 to 0.8 mm measured at its base (where the fringe joins the rim of the cup-shaped member). While four relatively large waves are shown in FIG. 6, if desired more waves and/or smaller waves may be used. The number and size of the waves are selected to provide desired product attributes.

Head 612 also differs from the designs described above in that the cup-shaped member 620 includes ribs 60 that are inclined with respect to the longitudinal axis of the cup-shaped member.

Figure 7:
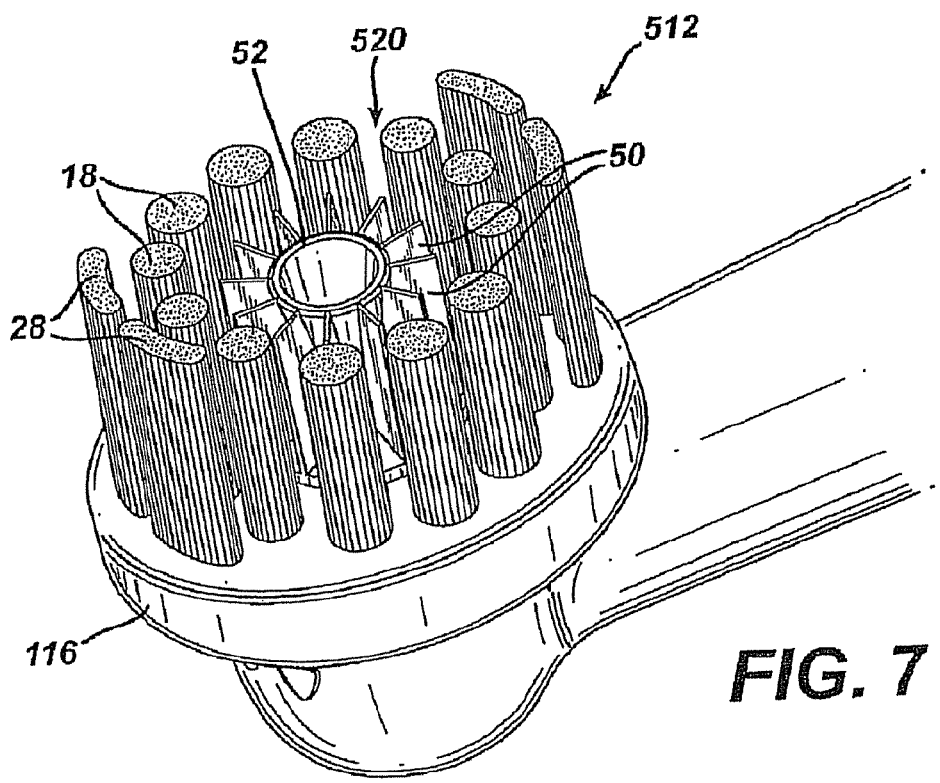
Figure 7A:
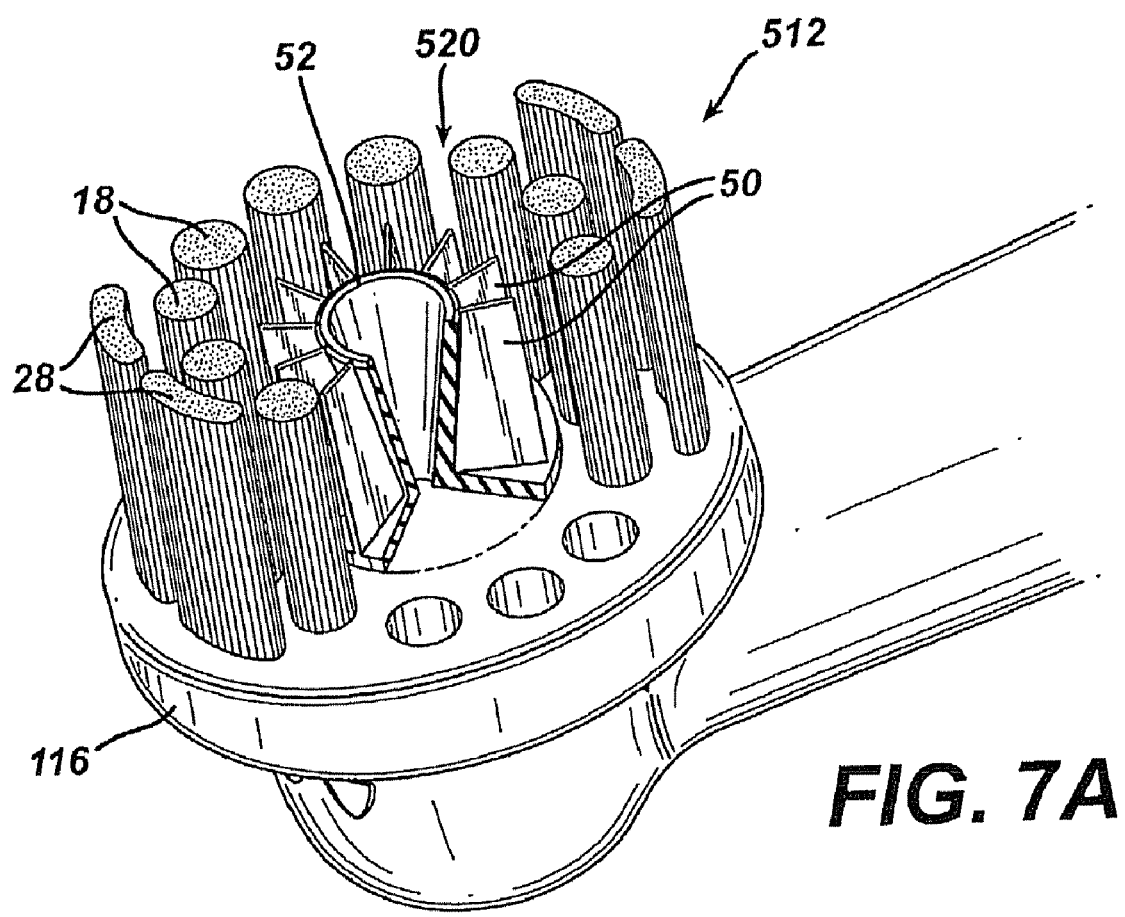

In the embodiment shown in FIG. 7, head 512 includes a fan-shaped member 520 that has a plurality of ribs 50 extending radially from an outer surface of its side wall 52 in a fan-like arrangement. In this embodiment, the side wall 52 is generally conical. Alternatively, if desired, the side wall may be cylindrical (not shown). In this embodiment, the fan-like structure of the cup-shaped member may enhance the foaming action of some toothpastes. The ribs may also act as "squeegees", enhancing tooth-cleaning action.

Figure 8:
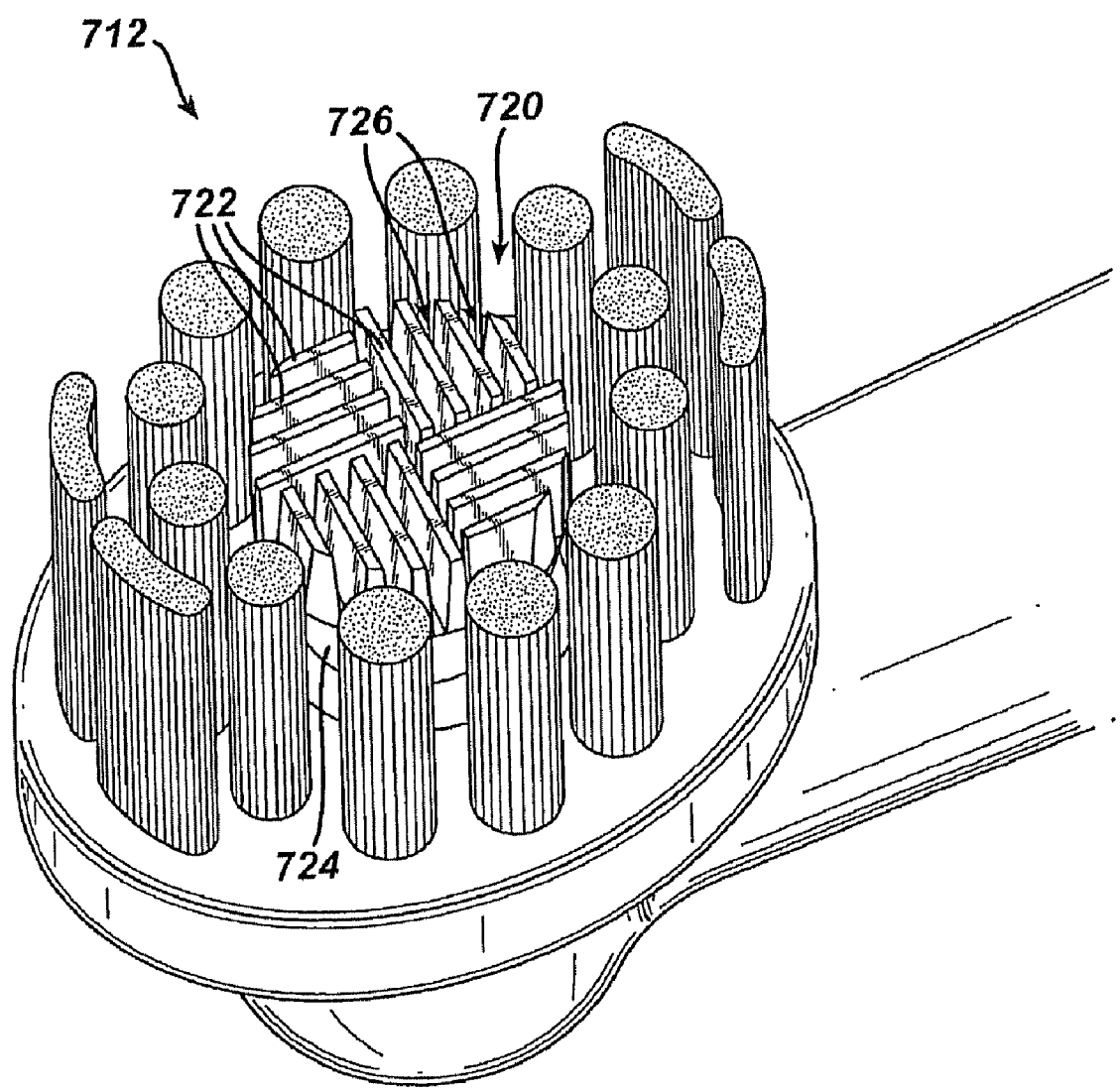

In the embodiment shown in FIG. 8, head 712 includes a textured member 720 that is comprised of a plurality of lammelae 722 that extend from a common base 724 together define a unitary structure. The lammelae 722 are arranged in different directions to give a "textured" feel. In this embodiment, the lammelae define a generally circular member, and are arranged in groups that are at right angles to each other in a "woven" pattern. However, the textured member may have any desired shape and arrangement of lamellae. It is generally preferred that the lammelae be relatively closely spaced, e.g., that spaces 726 be less than about 0.75 mm wide, more preferably about 0.5 mm or less.

Figure 9:
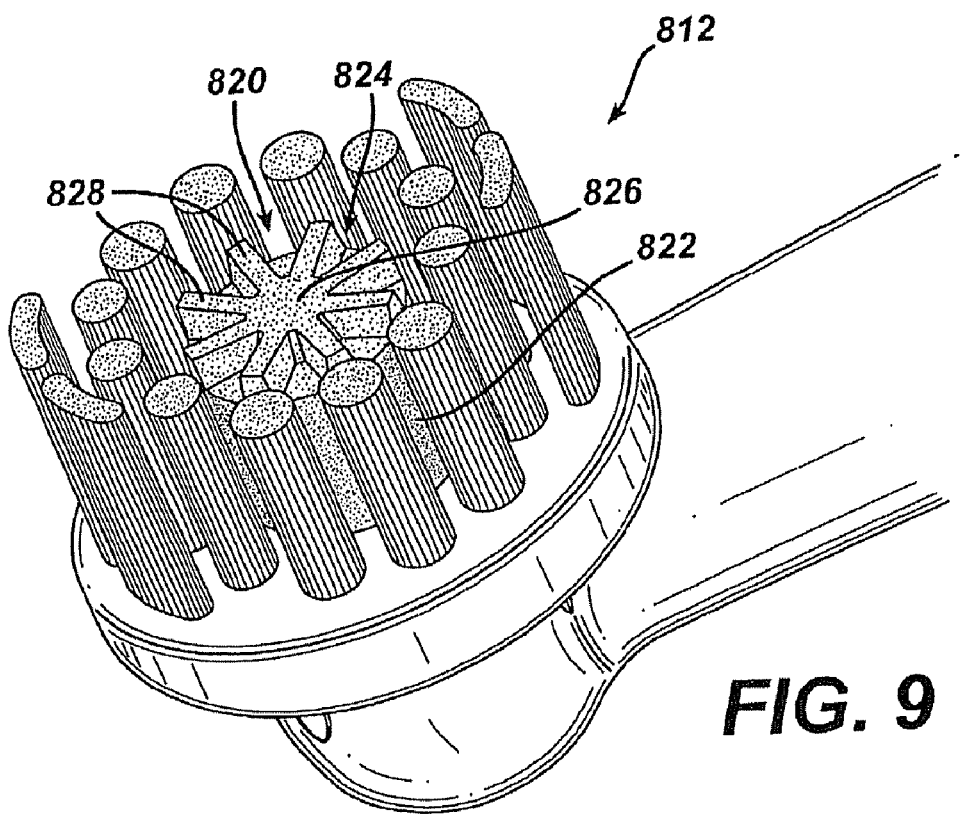

In the embodiment shown in FIG. 9, head 812 includes a textured member 820. Textured member 820 includes a generally cylindrical base 822 and, extending from the base, a contact portion 824 that includes a central hub 826 and a plurality of ribs 828 extending radially from the hub. Textured member 820 may be formed of a foam, as shown, to provide a surface texture.

Figure 10:
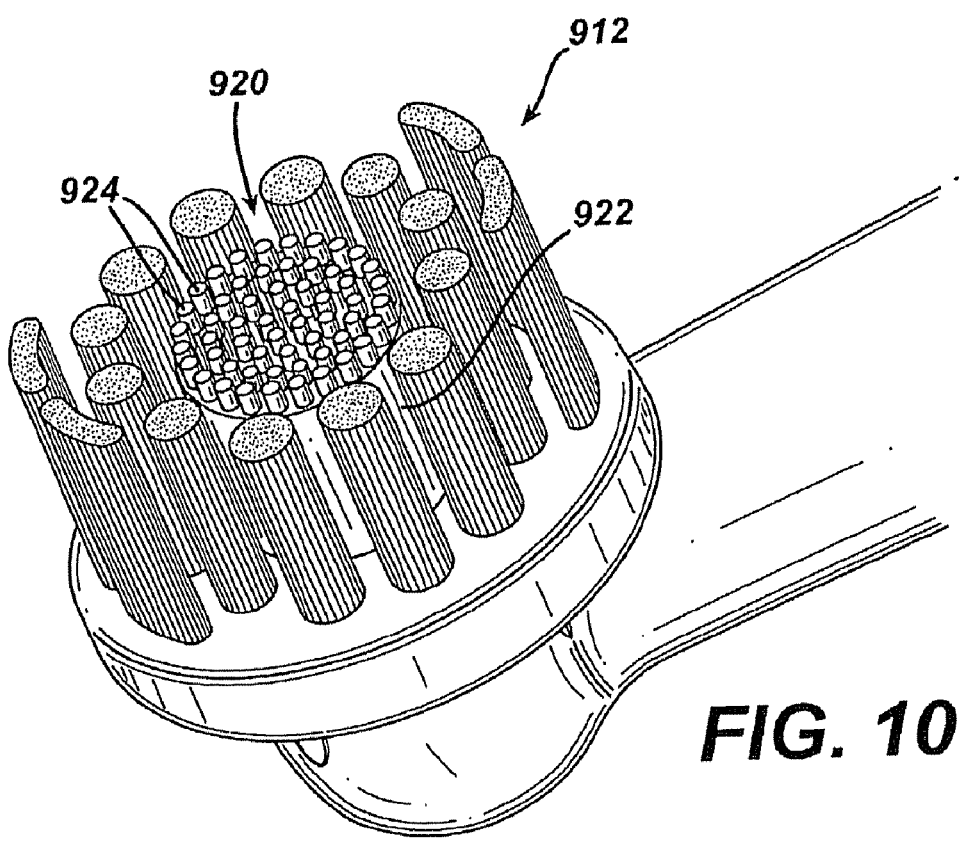

In the embodiment shown in FIG. 10, head 912 includes a textured member 920, including a generally cylindrical base 922 and, extending from the base, a plurality of small nubs 924 that provide the member with a textured feel.

A textured feel may be provided in many ways, for example by forming a resilient member of any desired shape of a material having a macroscopic surface texture, e.g., an open celled foam, or a material having texture-imparting particles embedded in its surface.

Other embodiments are within the scope of the following claims.

Figure 11:
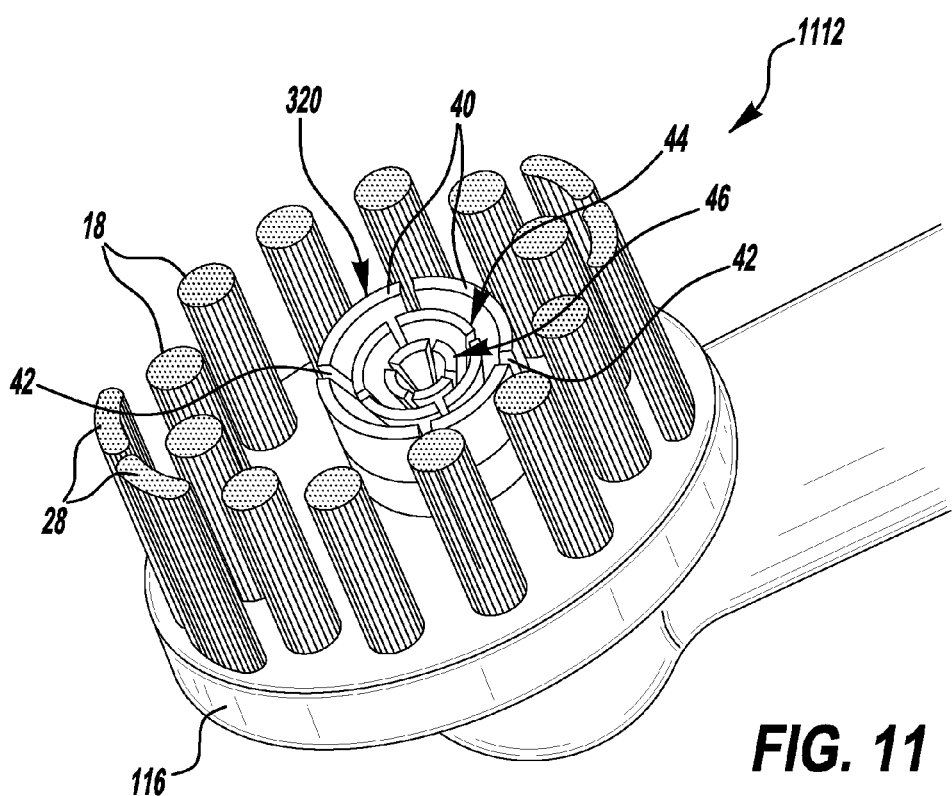

For example, while the cup-shaped member is shown in the drawings as centrally-located on the toothbrush head, if desired it may be positioned off-center. In FIGS. 2-10, the support members 116 are generally elliptical, rather than circular as shown in FIG. 1. FIG. 11 illustrates a generally elliptical head 116 having cup-shaped member 320, which is positioned off-center of the elliptical head. The remaining elements are substantially the same as the similarly identified elements described with reference to FIG. 4.

Moreover, while various embodiments are shown in the drawings and described above, many other types of cup-shaped members may be used, as will be well understood by those skilled in the art. For example, the side wall of the cup-shaped member may have a tapered outer surface, or may be straight sided or have any other desired design.

Additionally, which the cup-shaped member is described above as being surrounded on all sides by bristle tufts, if desired the cup-shaped member may be only partially surrounded by bristle tufts. For example, if desired the side tufts 18B in FIG. 1 could be omitted Moreover, while heads for power toothbrushes have been described above, resilient members having the features described above may be used on manual toothbrushes, if desired.

We claim:

1. A toothbrush, comprising:
a head sized to fit in an oral cavity, the head having a support structure;
a neck extending from the head;
a first plurality of upstanding arcuate elastomeric segments attached to the support structure, wherein the first plurality of upstanding arcuate elastomeric segments are arranged to define an open center area and wherein the first plurality of upstanding arcuate elastomeric segments are integrally connected;
a second plurality of upstanding arcuate elastomeric segments attached to the support structure, wherein the second plurality of upstanding arcuate elastomeric segments are arranged to define an open center area and wherein the second plurality of upstanding arcuate elastomeric segments are integrally connected;
a plurality of bristle tufts extending from the support structure and at least partially surrounding the first plurality of upstanding arcuate elastomeric segments,
wherein the head is elongated, and
wherein the plurality of bristle tufts include round bristle tufts and elongated bristle tufts,
wherein a first elongated bristle tuft is located on the distal end of the elongate head; and
a second elongated bristle tuft is located on the proximal end of the elongate head, and
wherein the first plurality of upstanding arcuate elastomeric segments comprise a first substantially circular arrangement, and the second plurality of upstanding arcuate elastomeric segments comprise a second substantially circular arrangement.

2. The toothbrush of claim 1, wherein the first and second pluralities of upstanding arcuate elastomeric segments are integrally connected by an elastomeric material.

3. The toothbrush of claim 1 wherein the elongated head has a longitudinal axis and the center of the first plurality of upstanding arcuate elastomeric segments is positioned along the longitudinal axis and offset from a central location of the elongated head.

4. The toothbrush of claim 3 wherein the second plurality of upstanding arcuate elastomeric segments is positioned along the longitudinal axis and off of the center of the elongated head.

5. The toothbrush of claim 1 wherein first plurality of upstanding arcuate elastomeric segments are concentric with the second plurality of upstanding arcuate elastomeric segments.

6. The toothbrush of claim 1 wherein the toothbrush is a power toothbrush.

7. The toothbrush of claim 1 wherein the outside walls of the first plurality of arcuate elastomeric segments arranged to form a first substantially circular pattern projects straight up away from the support structure.

8. The toothbrush of claim 7 wherein the inside walls of the first plurality of arcuate elastomeric segments are arranged to form a first substantially circular pattern that projects straight up away from the support structure.

9. The toothbrush of claim 8 wherein the outside walls of the second plurality of arcuate elastomeric segments arranged to form a second substantially circular pattern and projects straight up away from the support structure.

10. The toothbrush of claim 9 wherein the inside walls of the second plurality of arcuate elastomeric segments are arranged to form a second substantially circular pattern and project straight up away from the support structure.

11. The toothbrush of claim 1 further comprising at least one tooth cleaning element located within a central open area.

12. The toothbrush of claim 1 further comprising a tooth cleaning element located within each central open area.

13. A tooth cleaning device comprising:
an elongated head sized to fit in an oral cavity;
a neck extending from the head;
the head having a first surface;
the first surface having a midpoint located along a longitudinal axis of the head;
a resilient structure having a first plurality of curved segments arranged in a substantially circular pattern extending upward from the first surface;
the first plurality of curved segments being integrally joined to form a unitary structure;
wherein a center point of the substantially circular pattern of curved segments is positioned off of the midpoint of the first surface; and
a plurality of bristle tufts attached to the head and located outboard of the substantially circular pattern of curved segments
a second plurality of curved segments arranged in a substantially circular pattern extending upward from the first surface, the second plurality of curved segments being integrally joined to form a unitary structure
wherein the first plurality of curved segments and the second plurality of curved segments are integrally joined to form a unitary structure.

14. The tooth cleaning device of claim 13, further comprising a first pair of elongated bristle tufts, the first pair of elongated bristle tufts located on the distal end of the elongated head away from the neck and being separated from one another by an open area; and a second pair of elongated bristle tufts located on the proximal end of the head near the neck, the second pair of elongated bristle tufts being separated by an open area.

15. The tooth cleaning device of claim 13 wherein the curved segments have an inside wall that is substantially perpendicular to the first surface and an outside wall that is substantially perpendicular to the first surface.

16. The tooth cleaning device of claim 15 wherein the outside side of the curved segments wall is the same height as the inside wall of the curved segments.

17. The tooth cleaning device of claim 15 wherein the inside walls of the curved segments are parallel to the outside walls of the curved segments.

18. The tooth cleaning device of claim 13 wherein the top wiping edge of the plurality of curved segments are parallel with the first surface.

19. The tooth cleaning device of claim 13 wherein the second plurality of curved segments are positioned off of the midpoint of the first surface.

20. A tooth cleaning device comprising:
a head sized to fit in an oral cavity;
a neck extending from the head;
the head having an elongated first surface;
the first surface having a midpoint located along a longitudinal axis of the head;
a resilient structure having plurality of first curved segments extending upward from the first surface and arranged in a substantially first circular pattern;
wherein a center of the first substantially circular pattern is positioned off of the midpoint of the first surface;
the resilient structure having a plurality of second curved segments extending upward from the first surface and arranged in a substantially second circular pattern;
the resilient structure having plurality of third curved segments extending upward from the first surface and arranged in a substantially third circular pattern;
the plurality of first curved segments, second curved segments and third curved segments being integrally joined to form a single structure;
a plurality of round bristle tufts extending upward from the first surface and located outboard of at least one of the substantially circular patterns of curved segments;
a plurality of elongated bristle tufts extending upward from the first surface and located on the end of the elongate first surface away from the neck, and
a second plurality of elongated bristle tufts extending upward from the first surface located on the end of the elongate first surface near the neck.

21. The tooth cleaning device of claim 20, wherein the elongated bristle tufts have a substantially arcuate cross-sectional shape.

22. The tooth cleaning device of claim 20, wherein the at least one of the elongated bristle tufts is taller than at least one of the round bristle tufts.

23. The tooth cleaning device of claim 20, wherein the plurality of elongated bristle tufts extending upward from the first surface and located on the end of the elongate first surface away from the neck comprise two bristle tufts having arcuate shaped cross-sections.

24. The tooth cleaning device of claim 23, wherein the two bristle tufts having arcuate shaped cross-sections are separated by an open area.

25. The tooth cleaning device of claim 23, wherein the second plurality of elongated bristle tufts extending upward from the first surface and located on the end of the elongate first surface near the neck comprise two bristle tufts having arcuate shaped cross-sections.

26. The tooth cleaning device of claim 25, wherein the two bristle tufts having arcuate shaped cross-sections are separated by an open area.

27. The tooth cleaning device of claim 20 comprising at least two elongated bristle tufts having an arcuate cross-sectional shape that are located 180° apart from one another.

28. The tooth cleaning device of claim 20 wherein the plurality of first curved segments are concentric with the plurality of second curved segments.

29. The tooth cleaning device of claim 20 wherein the plurality of first curved segments comprises four segments.

30. The tooth cleaning device of claim 29 wherein the plurality of second curved segments comprises four segments.

31. The tooth cleaning device of claim 30 wherein the plurality of third curved segments comprises four segments.

32. The tooth cleaning device of claim 20 wherein at least one of the plurality of first curved segments borders at least one of the plurality of second curved segments.

33. The tooth cleaning device of claim 32 wherein at least one of the plurality of second curved segments borders at least one of the plurality of third curved segments.

34. The tooth cleaning device of claim 20 wherein the plurality of first curved segments, the plurality of second curved segments and the plurality of third curved segments comprise twelve curved segments.

35. The tooth cleaning device of claim 20 wherein at the plurality of first curved segments are surrounded by bristle tufts.

36. The tooth cleaning device of claim 20 wherein the plurality of round bristle tufts comprises twelve round bristle tufts.

37. The tooth cleaning device of claim 36 wherein the plurality of elongated bristle tufts comprises at least two elongated bristle tufts having an arcuate cross-sectional shape.

38. The tooth cleaning device of claim 20 wherein the plurality of round bristle tufts comprises at least twelve round bristle tufts, and the first plurality of curve segments comprises four curved segments, and the second plurality of curved segments comprises four curved segments, and the third plurality of curved segments comprises four curved segments.

39. The tooth cleaning device of claim 38, wherein the plurality of elongated bristle tufts extending upward from the first surface and located on the end of the elongate first surface away from the neck comprise two bristle tufts having arcuate shaped cross-sections that are separated by a space.

40. The tooth cleaning device of claim 39, wherein the second plurality of elongated bristle tufts extending upward from the first surface and located on the end of the elongate first surface near the neck comprise two bristle tufts having arcuate shaped cross-sections that are separated by a space.

41. The tooth cleaning device of claim 20 wherein the curved segments have an inside wall that is substantially perpendicular to the first surface and an outside wall that is substantially perpendicular to the first surface.

42. The tooth cleaning device of claim 41 wherein the outside side wall is the same height as the inside wall.

43. The tooth cleaning device of claim 20 wherein the top wiping edge of the plurality of curved segments are parallel with the first surface.

44. The tooth cleaning device of claim 20 wherein the second plurality of curved segments are positioned off of the midpoint of the first surface.

45. The tooth cleaning device of claim 20 wherein the inside walls of the first plurality of curved segments border a tooth cleaning element and the outside walls of the first plurality of curved segments border a tooth cleaning element.

46. A tooth cleaning device comprising:
an elongated head sized to fit in an oral cavity;
a neck extending from the elongated head;
the elongated head having a first surface;
a unitary resilient member having a plurality of substantially circular cups extending upward from the top surface;
the substantially circular cups each having a plurality of grooves located in the side walls forming a discontinuous top wiping edges; and
a plurality of bristle tufts extending upward from the first surface and located outboard of the plurality of substantially circular cups,
wherein the center of at least one substantially circular cups is offset from a midpoint of the elongated head.

47. The tooth cleaning device of claim 46 comprising three circular cups.

48. The tooth cleaning device of claim 47 comprising at least twelve discontinuous top wiping edges.

49. The tooth cleaning device of claim 46 comprising a plurality of round bristle tufts and a plurality of elongated bristle tufts.

50. The tooth cleaning device of claim 49 wherein the plurality of elongated bristle tufts have arcuate shaped cross-sections.

51. The tooth cleaning device of claim 49 wherein the plurality of round bristle tufts comprises at least twelve round bristle tufts.

52. The tooth cleaning device of claim 46 comprising round bristle tufts wherein the number of round bristle tufts is equal to the number of discontinuous top wiping edges.

53. The tooth cleaning device of claim 46 wherein each of the plurality of circular cups has four discontinuous wiping edges.

54. The tooth cleaning device of claim 46 comprising at least twelve discontinuous wiping edges and at least twelve round bristle tufts.

55. The tooth cleaning device of claim 46 wherein at least a portion of the plurality of grooves do not extend to the bottom of the circular cups.

* * * * *